(12) United States Patent
Napolitano et al.

(10) Patent No.: US 12,036,289 B2
(45) Date of Patent: Jul. 16, 2024

(54) GADOLINIUM BEARING PCTA-BASED CONTRAST AGENTS

(71) Applicant: BRACCO IMAGING S.P.A., Milan (IT)

(72) Inventors: Roberta Napolitano, Albiano d'Ivrea (IT); Luciano Lattuada, Cassina de'Pecchi (IT); Zsolt Baranyai, Trieste (IT); Nicole Guidolin, Trieste (IT); Giuseppe Marazzi, Milan (IT)

(73) Assignee: BRACCO IMAGING S.P.A., Milan (IT)

( * ) Notice: Subject to any disclaimer, the term of this patent is extended or adjusted under 35 U.S.C. 154(b) by 625 days.

(21) Appl. No.: 17/199,122

(22) Filed: Mar. 11, 2021

(65) Prior Publication Data

US 2021/0196840 A1    Jul. 1, 2021

Related U.S. Application Data

(63) Continuation of application No. 16/766,619, filed as application No. PCT/EP2019/071075 on Aug. 6, 2019, now Pat. No. 10,973,934.

(30) Foreign Application Priority Data

Aug. 6, 2018   (EP) .................................... 18187422

(51) Int. Cl.
| | | |
|---|---|---|
| A61B 5/055 | (2006.01) | |
| A61K 49/10 | (2006.01) | |
| C07F 5/00 | (2006.01) | |
| C07D 471/08 | (2006.01) | |

(52) U.S. Cl.
CPC ............ *A61K 49/106* (2013.01); *C07F 5/003* (2013.01); *A61K 49/108* (2013.01); *C07D 471/08* (2013.01)

(58) Field of Classification Search
CPC ..... A61K 49/106; A61K 49/108; C07F 5/003; C07D 471/08
See application file for complete search history.

(56) References Cited

U.S. PATENT DOCUMENTS

| | | | |
|---|---|---|---|
| 6,440,956 B1 | 8/2002 | Port | |
| 8,114,863 B2 | 2/2012 | Port | |
| 10,973,934 B2 * | 4/2021 | Napolitano | C07F 5/003 |
| 2007/0098643 A1 | 5/2007 | Nachman et al. | |
| 2009/0214441 A1 | 8/2009 | Port | |
| 2016/0101196 A1 | 4/2016 | Medina et al. | |
| 2022/0062443 A1 | 3/2022 | Greneur et al. | |

FOREIGN PATENT DOCUMENTS

| | | |
|---|---|---|
| EP | 0992245 A1 | 4/2000 |
| EP | 1931673 B1 | 8/2012 |
| EP | 2988756 B1 | 3/2017 |
| WO | 2000075141 A1 | 12/2000 |
| WO | 2003074523 A2 | 9/2003 |
| WO | 2006100305 A2 | 9/2006 |
| WO | 2020148436 A1 | 7/2020 |

OTHER PUBLICATIONS

Aime et al., "Properties, Solution State Behavior, and Crystal Structures of Chelates of DOTMA," Inorg. Chem., 50:7955-7965 (2011).
Clough et al., "Ligand design strategies to increase stability of gadolinium-based magnetic resonance imaging contrast agents," Nat. Commun. 10:1420 (2019).
Experimental Report and Declaration of Expert Witness, filed Feb. 23, 2022, in European Patent No. 3687994.
Experimental Report, filed Aug. 2, 2021, in European Patent No. 3687994.
Hermann et al., "Gadolinium (III) complexes as MRI contrast agents: ligand design and properties of the complexes," Dalton Trans., 3027-3047 (2008).
Moreau et al., "Thermodynamic and Structural Properties of Eu3+, Gd3+ and Tb3+ Complexes with 1,4,7,10-Tetra(2-glutaryl)-1,4,7,10-tetraazacyclododecane in Solution: EXAFS, Luminescence, Potentiometric Studies, and Quantum Calculations," Eur. J. Inorg. Chem. 3007-3020 (2003).
Vander Elst et al., "Stereospecific binding of MRI contrast agents to human serum albumin: the case of Gd-(S)-EOB-DTPA (Eovist) and its (R) isomer," J. Biol. Inorg. Chem., 6:196-200 (2001).
Woods et al., "Correlation of Water Exchange Rate with Isomeric Composition in Diastereoisomeric Gadolinium Complexes of Tetra(carboxyethyl)dota and Related Macrocyclic Ligands," J. Am. Chem. Soc. 122:9781-9792 (2000).
Ashoorzadeh, A. et al., "Synthetic evaluation of an enantiopure tetrahydropyridine N-oxide. Synthesis of (+)-febrifugine," Tetrahedron, 65:4671-4680 (2009).
Baranyai, Z. et al., "Dissociation Kinetics of Open-chain and Macrocyclic Gadolinium(III)-Aminopolycarboxylate Complexes Related to Magnetic Resonance Imaging: Catalytic Effect of Endogenous Ligands," Chem. Eur. J., 18:16426-16435 (2012).
Fries, P. et. al., "P03277—A New Approach to Achieve High-Contrast Enhancement," Invest. Radiol., 50:835-842 (2015).
International Search Report and Written Opinion for PCT/EP2019/071075, dated Sep. 20, 2019.
Lausi, A. et al., "Status of the crystallography beamlines at Elettra," The European Physical Journal Plus, 130:1-8 (2015).
Moreau, J. et. al., "Thermodynamic and structural properties of Eu3+ complexes of a new 12-membered tetraaza macrocycle containing pyridine and N-glutaryl groups as pendant arms: characterization of three complexing successive phases," Dalton Transactions, 16:1611-1620 (2007).

(Continued)

*Primary Examiner* — Michael G. Hartley
*Assistant Examiner* — Melissa J Perreira
(74) *Attorney, Agent, or Firm* — VIVICAR Law, PLLC

(57) ABSTRACT

The present invention relates to the RRR/SSS pair of enantiomers of the of Gd(PCTA-tris-glutaric acid), the single enantiomers of the pair, the pharmaceutically acceptable salts thereof, their amide derivatives, and compositions comprising at least 50% of these compounds.

4 Claims, 9 Drawing Sheets

(56) References Cited

OTHER PUBLICATIONS

Sheldrick, G.M., "SHELXT—Integrated space-group and crystal-structure determination," Acta Crystallographica Section A, 71:3-8 (2015).
Tircso, G. et al., "Equilibrium and Formation/Dissociation Kinetics of Some LnIIIPCTA Complexes," Inorg Chem., 45:9269-80 (2006).

* cited by examiner

Figure 6/11

AREA OF A (◇), B(□), C (△) and D (○) PEAKS IN THE HPLC CHROMATOGRAM OF Gd(PCTA-tris-glutaric acid). THE OPEN SYMBOLS AND CURVES REPRESENT THE EXPERIMENTAL AND THE CALCULATED AREA VALUES, RESPECTIVELY.

([GdL]=0.2 mM, 1.0 M HCl, 25°C)

TOTAL AREA IN THE HPLC CHROMATOGRAM OF P03277 (◇) OVER TIME. AREA IN THE HPLC CHROMATOGRAM OF THE ENANTIOMERS PAIR C FUNCTIONALIZED WITH R ISOSERINOL (□), S ISOSERINOL (△) AND RACEMIC-ISOSERINOL (○) OVER TIME. THE OPEN SYMBOLS AND CURVES REPRESENT THE EXPERIMENTAL AND THE CALCULATED AREA VALUES, RESPECTIVELY. ([GdL]=0.2 mM, 1.0 M HCl, 25°C)

|  | RRR - RRR | RRR - SSS |
|---|---|---|
| Abundance | 28 % | 22 % |
|  | SSS - RRR | SSS-SSS |
| Abundance | 22 % | 28% |

GADOLINIUM BEARING PCTA-BASED CONTRAST AGENTS

CROSS-REFERENCE TO RELATED APPLICATIONS

This application is a continuation of U.S. application Ser. No. 16/766,619, filed May 22, 2020, which is the national stage application of corresponding international application number PCT/EP2019/071075, filed Aug. 6, 2019, which claims priority to and the benefit of European application no. 18187422.3, filed Aug. 6, 2018, all of which are hereby incorporated by reference in their entirety.

FIELD OF THE INVENTION

The present invention generally relates to the field of Magnetic Resonance Imaging (MRI). More in particular, it relates to isomers of PCTA-based contrast agents, and to MRI contrast agents enriched with these isomers.

BACKGROUND OF THE INVENTION

MRI contrast agents used in daily diagnostic practice typically include gadolinium complex compounds characterized by high stability constants that guarantee against the in vivo release of the free metal ion (that is known to be extremely toxic for living organisms).

Another key parameter in the definition of the tolerability of a gadolinium-based contrast agent is the kinetic inertness (or kinetic stability) of Gd(III)-complex, that is estimated through the half-life ($t_{1/2}$) of the dissociation (i.e. decomplexation) of the complex.

A high inertness becomes crucial in particular for those complex compounds having lower thermodynamic stability and/or longer retention time before excretion, in order to avoid or minimize possible decomplexation or transmetallation reactions.

EP1931673 (Guerbet) discloses PCTA derivatives of formula

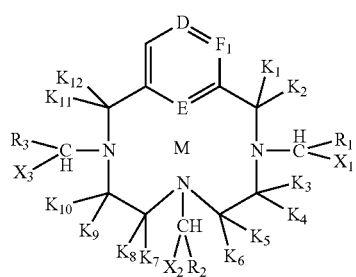

(I)

and a synthetic route for their preparation.

EP 2988756 (same Applicant) discloses a pharmaceutical composition comprising the above derivatives together with a calcium complex of 1,4,7,10-tetraazacyclododecane-1,4,7,10-tetraacetic acid. According to the EP 2988756, the calcium complex compensates the weak thermodynamic stability observed for PCTA-based gadolinium complexes, by forming, through transmetallation, a strong complex with free lanthanide ion, thereby increasing the tolerability of the contrast agent.

Both EP1931673 and EP 2988756 further refer to enantiomers or diastereoisomers of the claimed compounds, or mixture thereof, preferentially chosen from the RRS, RSR, and RSS diastereoisomers.

Both the above patents disclose, among the specific derivatives, (α3, α6, α9)-tris(3-((2,3-dihydroxypropyl)amino)-3-oxopropyl)-3,6,9,15-tetraazabicyclo(9.3.1)pentadeca-1(15),11,13-triene-3,6,9-triacetato(3-)-(κN3,κN6, κN9,κN15,κO3,κO6,κO9)gadolinium, more recently identified as gadolinium chelate of 2,2',2''-(3,6,9-triaza-1(2,6)-pyridinacyclodecaphane-3,6,9-triyl)tris(5-((2,3-dihydroxypropyl)amino)-5-oxopentanoic acid), (CAS registry number: 933983-75-6), having the following formula

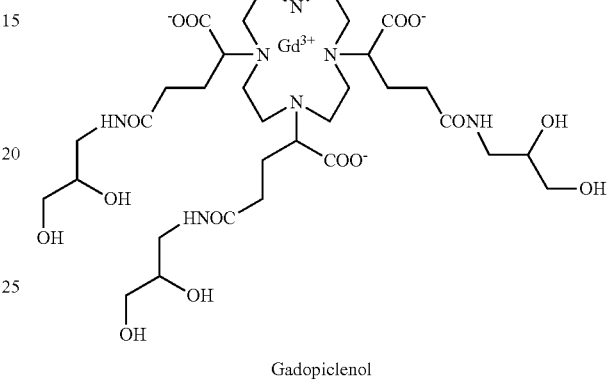

Gadopiclenol otherwise identified as P03277 or Gadopiclenol.

For Gadopiclenol, EP1931673 reports a relaxivity of 11 $mM^{-1}s^{-1}Gd^{-1}$ (in water, at 0.5 T, 37° C.) while EP 2988756 reports a thermodynamic equilibrium constant of $10^{-14.9}$ (log $K^{term}$=14.9).

Furthermore, for this same compound a relaxivity value of 12.8 $mM^{-1}s^{-1}$ in human serum (37° C., 1.41 T), stability (log $K^{term}$) of 18.7, and dissociation half-life of about 20 days (at pH 1.2; 37° C.) have been reported by the proprietor (Investigative Radiology 2019, Vol 54, (8), 475-484).

The precursor for the preparation of the PCTA derivatives disclosed by EP1931673 (including Gadopiclenol) is the Gd complex of the 3,6,9,15-tetraazabicyclo-[9.3.1]pentadeca-1(15),11,13-triene-tri(α-glutaric acid) having the following formula

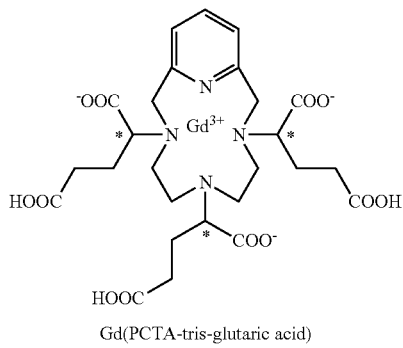

Gd(PCTA-tris-glutaric acid)

herein identified as "Gd(PCTA-tris-glutaric acid)". In particular, Gadopiclenol is obtained by amidation of the above compound with isoserinol.

As observed by the Applicant, Gd(PCTA-tris-glutaric acid) has three stereocenters on the glutaric moieties (identified with an asterisk (*) in the above structure) that lead to a $2^3=8$ possible stereoisomers. More particularly, the above structure can generate four pairs of enantiomers, schematized in the following Table 1

TABLE 1

| RRR | SSS |
|---|---|
| RSR | SRS |
| RRS | SSR |
| RSS | SRR |

Isomer RRR is the mirror image of isomer SSS and that is the reason why they are called enantiomers (or enantiomer pairs). As known, enantiomers display the same physico-chemical properties and are distinguishable only using chiral methodologies, such as chiral chromatography or polarized light.

On the other hand, isomer RRR is neither equal to nor is it the mirror image of any of the other above six isomers; these other isomers are thus identified as diastereoisomers of the RRR (or SSS) isomer. Diastereoisomers may display different physicochemical properties, (e.g., melting point, water solubility, relaxivity, etc.).

Concerning Gadopiclenol, its chemical structure contains a total of six stereocenters, three on the glutaric moieties of the precursor as above discussed and one in each of the three isoserinol moieties attached thereto, identified in the following structure with an asterisk (*) and with an empty circle (°), respectively:

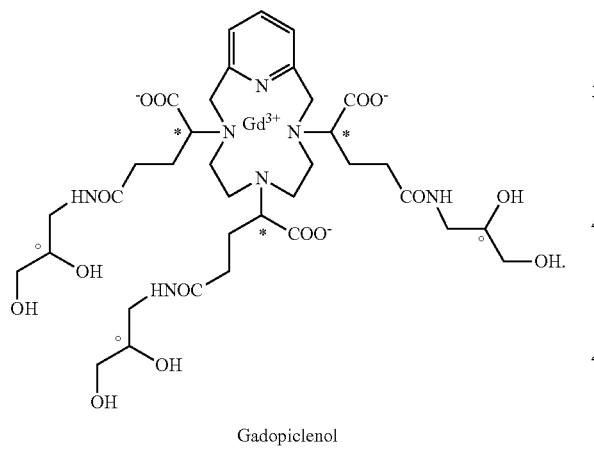

Gadopiclenol

This leads to a total theoretical number of $2^6=64$ stereoisomers for this compound.

However, neither EP1931673 nor EP 2988756 describe the exact composition of the isomeric mixture obtained by following the reported synthetic route, nor does any of them provide any teaching for the separation and characterization of any of these isomers, or disclose any stereospecific synthesis of Gadopiclenol.

SUMMARY OF THE INVENTION

The applicant has now found that specific isomers of the above precursor Gd(PCTA-tris-glutaric acid) and of its derivatives (in particular Gadopiclenol) possess improved physico-chemical properties, among other in terms of relaxivity and kinetic inertness.

An embodiment of the invention relates to a compound selected from the group consisting of:

the enantiomer [(αR,α'R,α"R)-α,α',α"-tris(2-carboxyethyl)-3,6,9,15-tetraazabicyclo[9.3.1]pentadeca-1(15),11,13-triene-3,6,9-triacetato(3-)-κN3,κN6,κN9,κN15,κO3,κO6,κO9]-gadolinium (RRR enantiomer) having the formula (Ia):

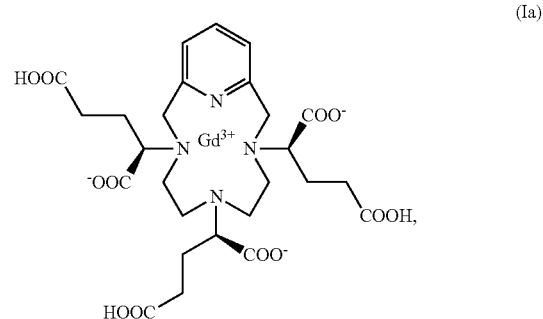

(Ia)

the enantiomer [(αS,α'S,α"S)-α,α',α"-tris(2-carboxyethyl)-3,6,9,15-tetraazabicyclo-[9.3.1]pentadeca-1(15),11,13-triene-3,6,9-triacetato(3-)κN3,κN6,κN9,κN15,κO3,κO6,κO9]-gadolinium (SSS enantiomer) having the formula (Ib):

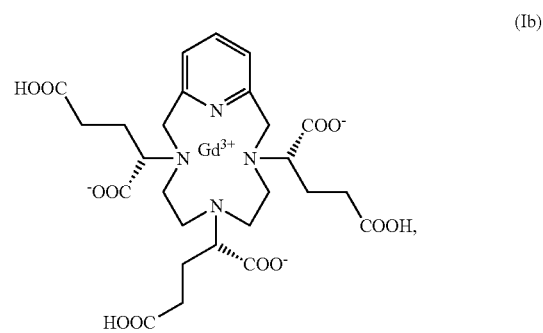

(Ib)

the mixtures of such RRR and SSS enantiomers, and a pharmaceutically acceptable salt thereof.

Another embodiment of the invention relates to an isomeric mixture of Gd(PCTA-tris-glutaric acid) comprising at least 50% of the RRR isomer [(αR,α'R,α"R)-α,α',α"-tris(2-carboxyethyl)-3,6,9,15-tetraazabicyclo[9.3.1]pentadeca-1(15),11,13-triene-3,6,9-triacetato(3-)-κN3,κN6,κN9,κN15,κO3,κO6,κO9]-gadolinium, of formula (Ia), or of the SSS isomer [(αS,α'S,α"S)-α,α',α"-tris(2-carboxyethyl)-3,6,9,15-tetraazabicyclo[9.3.1]pentadeca-1(15),11,13-triene-3,6,9-triacetato(3-)-κN3,κN6,κN9,κN15,κO3,κO6,κO9]-gadolinium of formula (Ib), or of a mixture thereof, or a pharmaceutically acceptable salt thereof.

Another aspect of the invention relates to the amides obtained by conjugation of one of the above compounds or isomeric mixture with an amino group, e.g. preferably, serinol or isoserinol.

An embodiment of the invention relates to an amide derivative of formula (II A)

$$F(NR_1R_2)_3 \quad \quad \quad (II\,A)$$

in which:

F is:

a RRR enantiomer residue of formula IIIa

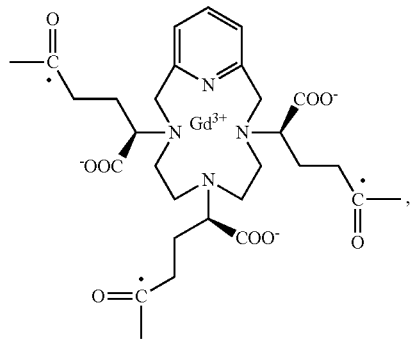

a SSS enantiomer residue of formula IIIb

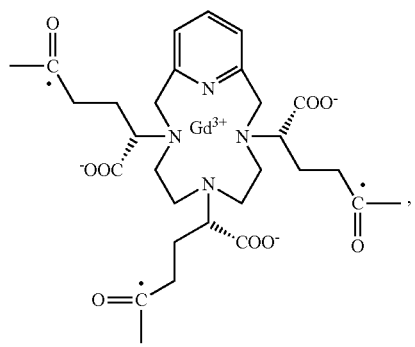

or a mixture of such RRR and SSS enantiomer residues;

and each of the three —NR$_1$R$_2$ group is bound to an open bond of a respective carboxyl moiety of F, identified with a full circle (●) in the above structures;

R$_1$ is H or a C$_1$-C$_6$ alkyl, optionally substituted by 1-4 hydroxyl groups;

R$_2$ is a C$_1$-C$_6$ alkyl optionally substituted by 1-4 hydroxyl groups, and preferably a C$_1$-C$_3$ alkyl substituted by one or two hydroxyl groups.

Another embodiment of the invention relates to an isomeric mixture of an amide derivative of Gd(PCTA-tris-glutaric acid) having the formula (II B)

F'(NR$_1$R$_2$)$_3$    (II B)

in which:

F' is an isomeric mixture of Gd(PCTA-tris-glutaric acid) residue of formula (III)

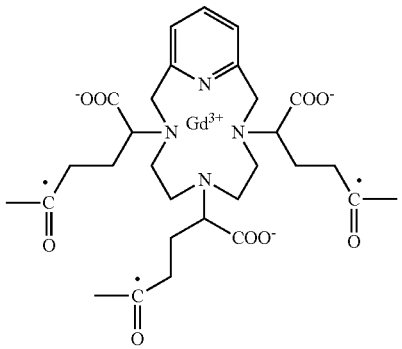

said isomeric mixture of the Gd(PCTA-tris-glutaric acid) residue comprising at least 50% of an enantiomer residue of the above formula (IIIa), of the enantiomer residue of the above formula (IIIb), or of a mixture thereof; and each of the —NR$_1$R$_2$ groups is bound to an open bond of a respective carboxyl moiety of F', identified with a full circle (●) in the above structure, and is as above defined for the compounds of formula (II A).

A further aspect of the invention relates to a pharmaceutically acceptable salt of the RRR or SSS enantiomers of the of Gd(PCTA-tris-glutaric acid) or, preferably, of a RRR/SSS mixture thereof, or of an isomeric mixture of Gd(PCTA-tris-glutaric acid) comprising at least 50% of any of these enantiomers or RRR/SSS enantiomers mixtures, or an amide derivative thereof of the above formula (II A) or (II B) for use as MRI contrast agent, in particular for the diagnostic imaging of a human or animal body organ or tissue by use of the MRI technique.

A further aspect relates to a pharmaceutically acceptable composition comprising at least one compound or isomeric mixture according to the invention, or a pharmaceutically acceptable salt or amide derivative thereof as defined above, in admixture with one or more physiologically acceptable carriers or excipient.

In another aspect, the invention relates to a stereoselective synthesis of the RRR or SSS isomer of the Gd(PCTA-tris-glutaric acid), or of a salt thereof.

An embodiment of the invention relates to a process for the synthetic preparation of an amide derivative of formula (II A)

F(NR$_1$R$_2$)$_3$    (II A)

where F, R$_1$ and R$_2$ are as above said, which comprises:

a) obtaining the RRR, or the SSS isomer of the Gd(PCTA-tris-glutaric acid) complex, or a mixture thereof; and b) converting the isomer, or mixture of isomers obtained from step a) in the amide derivative thereof;

as well as to a process for the preparation of an isomeric mixture of an amide derivative of the above formula (II B) which comprises:

a') obtaining an isomeric mixture of the Gd(PCTA-tris-glutaric acid) comprising at least 50% of the enantiomer RRR, or SSS, or of a mixture thereof;

b') converting the isomeric mixture of the Gd(PCTA-tris-glutaric acid) obtained from step a') in the corresponding isomeric mixture of respective amide derivative.

DETAILED DESCRIPTION OF THE INVENTION

The synthetic process disclosed by the prior-art, (see U.S. Pat. No. 6,440,956 cited by EP1931673) allows to obtain Gd(PCTA-tris-glutaric acid) as a mixture of isomers (herein otherwise identified as "isomeric mixture of Gd(PCTA-tris-glutaric acid)"), appreciable as several peaks in HPLC.

A preparative HPLC method has been prompted, allowing to separate four peaks from the mixture, which have same m/z ratio (Gd(H$_4$L)+:752.14 m/z).

Figure 1:
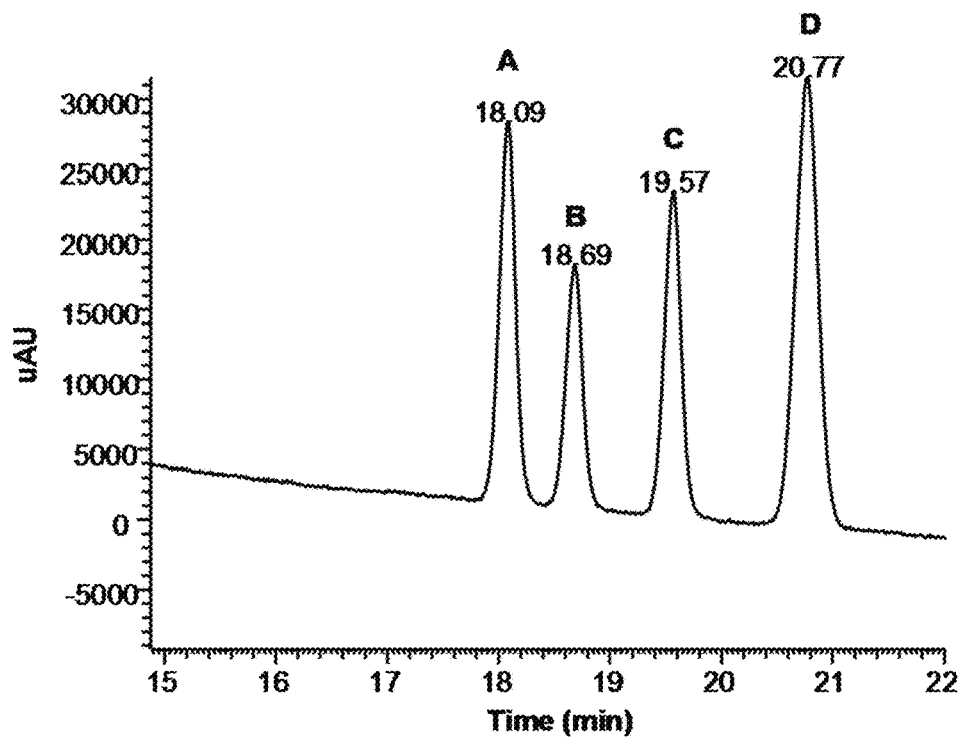
FIG. 1 shows the HPLC chromatogram of the Gd(PCTA-tris-glutaric acid) collected as an isomeric mixture from Example 1, carried out by following the synthetic procedure disclosed by the prior art ([GdL]=0.2 mM, 25° C.).

A representative chromatogram of the resolved isomeric mixture is shown in FIG. 1, where each peak, for convenience identified by a letter, A, B, C, and D respectively, is reasonably ascribable to one of the above identified pairs of enantiomers. More precisely, each peak is related to a pair of enantiomers, characterized by the same m/z ratio in MS spectra that cannot be further discriminated with normal reverse phase HPLC.

We have now unexpectedly found that the enantiomers pair related to the peak C of the HPLC chromatogram, (or enantiomers pair C, as hereinafter used interchangeably) shows optimal properties, especially in terms of kinetic inertness and reduced tendency to release Gd.

For instance, we found that the enantiomers pair C has a dissociation half-life (in 1M HCl) some tens of times higher with respect to the one of the enantiomers pair associated with peak B, and more than ten times higher than the average half-life of the Gd(PCTA-tris-glutaric acid) isomeric mixture.

Moreover, the relaxivity value associated with the enantiomers pair related to peak C is significantly higher than the one reported in 1931673 B1 for the isomeric mixture of the Gd(PCTA-tris-glutaric acid), tested at the same conditions.

This enantiomers pair C proved to comprise: [(αR,α'R,α"R)-α,α',α"-tris(2-carboxyethyl)-3,6,9,15-tetraazabicyclo[9.3.1]pentadeca-1(15),11,13-triene-3,6,9-triacetato(3-)-κN3,κN6,κN9,κN15,κO3,κO6,κO9]-gadolinium, namely the isomer RRR of the Gd(PCTA-tris-glutaric acid) of formula (Ia)

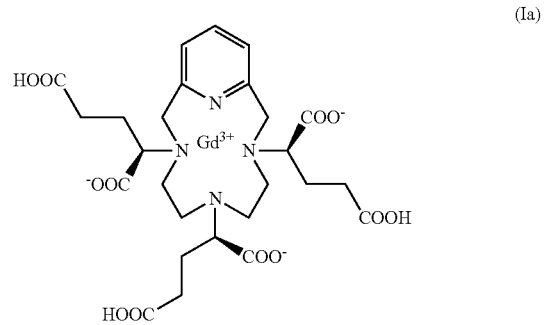

(Ia)

and the respective mirror isomer [(αS,α'S,α"S)-α,α',α"-tris(2-carboxyethyl)-3,6,9,15-tetraazabicyclo[9.3.1]pentadeca-1(15),11,13-triene-3,6,9-triacetato(3-)-κN3,κN6,κN9,κN15,κO3,κO6,κO9]-gadolinium, namely the SSS isomer of the Gd(PCTA-tris-glutaric acid) of formula (Ib)

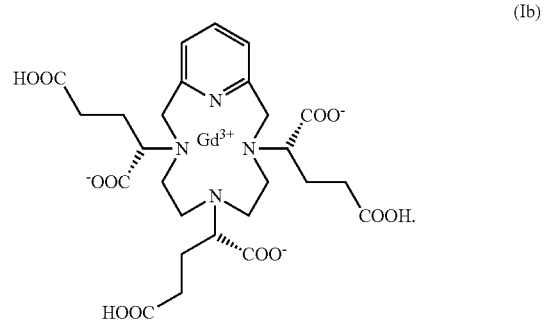

(Ib)

Surprisingly, the improved properties displayed by the individual enantiomers (RRR and SSS) and the RRR/SSS enantiomers pair of Gd(PCTA-tris-glutaric acid) (or RRR/SSS Gd(PCTA-tris-glutaric acid), as hereinafter used interchangeably) are unexpectedly substantially maintained even after its conjugation, e.g. leading to achieve amide derivatives thereof.

For instance, the coupling reaction of RRR/SSS Gd(PCTA-tris-glutaric acid) and, likewise, of each individual RRR or SSS enantiomer thereof with isoserinol, leads to a final amide derivative having same molecular formula of Gadopiclenol. In this regard, it is interesting to note that, regardless of the type of isoserinol used, whether it is the R or S isomer, or the racemic isoserinol, its conjugation with the RRR/SSS enantiomers of Gd(PCTA-tris-glutaric acid) leads to respective amide derivatives that have the same retention time and are, therefore, indistinguishable by normal reverse phase HPLC.

Thus, the different isomeric form of the appended isoserinol (or, more generally, of amine derivative), does not affect the major properties of the final conjugate compound that are essentially determined by the stereochemistry of the Gd(PCTA-tris-glutaric acid) precursor.

Indeed, the improved properties shown by the enantiomers pair related to the peak C with respect to the isomeric mixture of the Gd(PCTA-tris-glutaric acid) are substantially maintained after the conjugation thereof with isoserinol, regardless of the configuration of the coupled isoserinol.

In particular, regardless of the configuration of the isoserinol, its coupling with the RRR/SSS enantiomers pair of Gd(PCTA-tris-glutaric acid) leads to an amide compound having greater kinetic inertness and relaxivity compared to Gadopiclenol obtained as an isomeric mixture with the synthetic procedure of the prior art.

In the present description, and unless otherwise provided, the expression "isomeric mixture" (referred to a specific compound) includes within its meaning a mixture comprising at least two stereoisomers of this compound. In particular, when used with reference to Gd(PCTA-tris-glutaric acid), the expression "isomeric mixture" refers to a non-separated mixture of at least two of the 8 diastereomers (or diastereoisomers, as herein used interchangeably) and, more precisely, 4 enantiomers pairs generated by the three stereocenters contained in the molecule, and identified in Table 1. On the other hand, when used with reference to an amide derivative of the Gd(PCTA-tris-glutaric acid) such as, for instance, Gadopiclenol, the expression "isomeric mixture" refers to an undefined and non-separated mixture of the respective amide derivative of the above at least two (of the four possible) enantiomers pairs of the Gd(PCTA-tris-glutaric acid) residue.

To this extent, as each of the of the amine groups of the amide derivative may in turn contain one or more stereocenters, the total number of possible stereoisomers of the amide derivative may correspondingly increase. For instance, the conjugation of Gd(PCTA-tris-glutaric acid) with three molecules of isoserinol, each having a respective stereocenter, brings up to 64 the number of possible stereoisomers (32 enantiomer pairs) of the corresponding amide derivative, generated by the presence of the respective total six stereocenters on the molecule.

In the present description and claims, the expressions "isomeric mixture of an amide derivative of Gd(PCTA-tris-glutaric acid)" or "amide derivative of an isomeric mixture of Gd(PCTA-tris-glutaric acid)" are used interchangeably.

The expression "enantiomers C" refers to the pair of enantiomers related to the peak C, as per FIG. 1. Said enantiomers C correspond to the RRR/SSS enantiomers pair of the Gd(PCTA-tris-glutaric acid).

The expression "RRR/SSS enantiomers pair" (or RRR/SSS enantiomers) generally refers to a mixture of the enantiomer RRR and respective mirror isomer SSS of an intended compound, including a racemic mixture thereof. In the present description, this expression is typically used with reference to the Gd(PCTA-tris-glutaric acid), and refers to a mixture of the enantiomers RRR and SSS of this compound (or RRR/SSS mixture thereof). More particularly, the expression "RRR/SSS enantiomers pair of the Gd(PCTA-tris-glutaric acid)" (or "RRR/SSS Gd(PCTA-tris-glutaric acid)" as used herein interchangeably) refers to a mixture of [(αR,α'R,α"R)-α,α',α"-tris(2-carboxyethyl)-3,6,9,15-tetraazabicyclo[9.3.1]pentadeca-1(15),11,13-triene-3,6,9-triacetato(3-)-κN3,κN6,κN9,κN15,κO3,κO6,κO9]-gadolinium (RRR enantiomer) and [(αS,α'S,α"S)-α,α',α"-tris(2-carboxyethyl)-3,6,9,15-tetraazabicyclo[9.3.1]pentadeca-1(15),11,13-triene-3,6,9-triacetato(3-)-κN3,κN6,κN9,κN15,κO3,κO6,κO9]-gadolinium (SSS enantiomer), e.g. schematized below

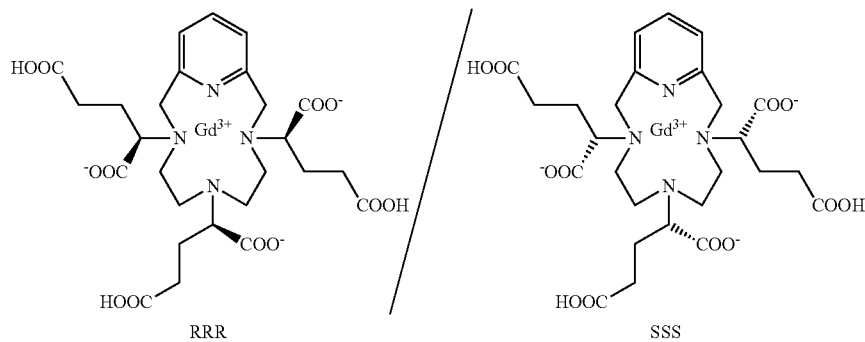

RRR        SSS

The expression "compound D'" refers to the amide derivative obtained by the coupling reaction of the RRR/SSS Gd(PCTA-tris-glutaric acid) with isoserinol.

The expression "stereoselective synthesis" (or "asymmetric synthesis" herein used interchangeably), comprises within its meaning a chemical reaction (or reaction sequence) in which one or more new elements of chirality are formed in a substrate molecule and which produces the stereoisomeric (enantiomeric or diastereoisomeric) products in unequal amounts. In the present description the expression "stereoselective synthesis" is used in particular with reference to the RRR and respective mirror isomer SSS of the Gd(PCTA-tris-glutaric acid), and refers to a synthesis allowing to obtain a complex containing at least 55%, preferably 65%, more preferably 75%, and most preferably at least 85% of any of the two enantiomers.

The term "pharmaceutically acceptable salt", as used herein, refers to derivatives of the compounds of the invention wherein the parent compound is suitably modified by converting any of the free acid or basic groups, if present, into the corresponding addition salt with any base or acid conventionally intended as being pharmaceutically acceptable.

Preferred cations of inorganic bases which can be suitably used to prepare a salt of the invention comprise, for instance, ions of alkali or alkaline-earth metals such as potassium, sodium, calcium or magnesium.

Preferred cations of organic bases comprise, for instance, those of primary, secondary and tertiary amines such as, for instance, ethanolamine, diethanolamine, morpholine, glucamine, N-methylglucamine, N,N-dimethylglucamine.

Preferred cations and anions of amino acids comprise, for instance, those of taurine, glycine, lysine, arginine, ornithine or of aspartic and glutamic acids.

Moreover, the terms "moiety" or "moieties", "residue" or "residues" are herewith intended to define the residual portion of a given molecule once properly attached or conjugated, either directly or through any suitable linker, to the rest of the molecule.

For instance, when used with reference to amide derivatives of Gd(PCTA-tris-glutaric acid) (either in the form of an isomeric mixture or of the RRR or SSS isomer, or RRR/SSS enantiomers mixture or enantiomers pair of the same), the term "residue" refers to the portion the Gd(PCTA-tris-glutaric acid) which is attached to the amine groups to give the corresponding amide derivative.

In particular, the term "residue of the isomeric mixture of Gd(PCTA-tris-glutaric acid)" refers to a compound having the following formula (III)

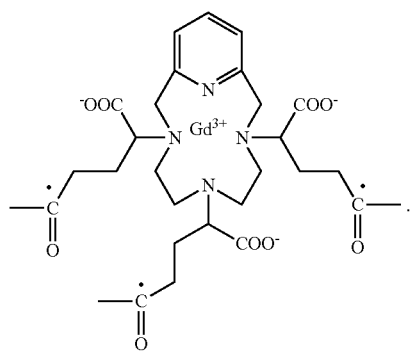

III

This residue may be conjugated, for instance, with amino residues of formula —NR$_1$R$_2$ through the open bonds of the carboxyl moieties identified with a full circle (●) in the above structure, to give the corresponding amide derivative of formula

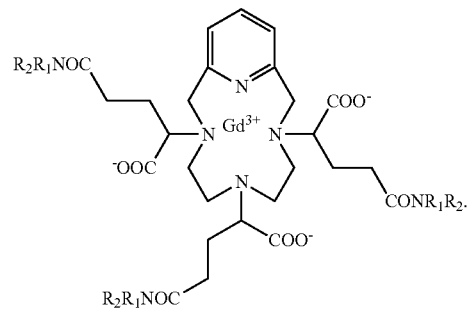

Similarly, the term "residue of the RRR and SSS enantiomers of the Gd(PCTA-tris-glutaric acid)" refers to compounds having, respectively, the following formula (IIIA)

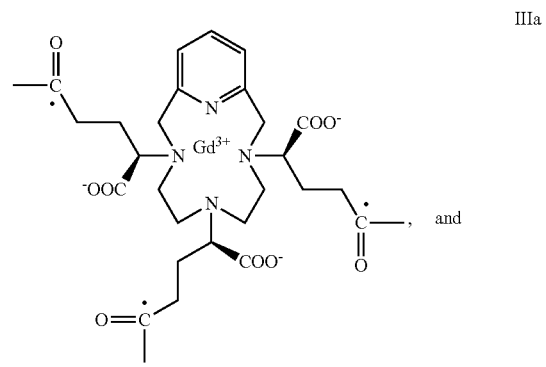

IIIa

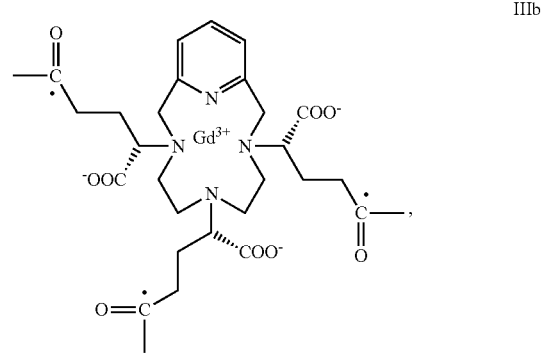

IIIb

The term "residue" similarly applies to the corresponding residues of the RRR/SSS enantiomers pair, or, in general, of enantiomers mixtures.

A preparative HPLC method has been prompted, allowing to separate four peaks from the Gd(PCTA-tris-glutaric acid) obtained by following the non-stereoselective synthesis disclosed by the prior-art, for convenience identified as A, B, C and D, respectively, having same m/z ratio (Gd(H$_4$L)+: 752.14 m/z). By taking into account the three stereocenters present in the molecule (identified as asterisks in above molecular structure), the four signals in the HPLC chromatograms of Gd(PCTA-tri-glutaric acid) complex have been assigned to the respective four enantiomer pairs formed with the different optical isomers of glutaric acid residue, formerly identified in Table 1.

In order to investigate the kinetic inertness of the racemic mixture of the Gd(PCTA-tris-glutaric acid) and, particularly, of the four enantiomer pairs thereof separated by HPLC, we investigated their dissociation reactions taking place under acidic conditions. A large excess of H⁺ ([HCl]=1.0 M) was in particular exploited in order to guarantee the pseudo-first order kinetic conditions.

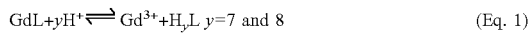

$$GdL + yH^+ \rightleftharpoons Gd^{3+} + H_yL \quad y=7 \text{ and } 8 \qquad (Eq. 1)$$

where L is the the protonated PCTA-tri-glutaric acid (free ligand), and y is the number of protons attached to the ligand.

A solution of Gd(PCTA-tris-glutaric acid) (isomeric mixture) in 1 M HCl was prepared and was analysed over the time as explained in Example 7.

In particular, the area value for each of the A, B, C, and D peaks was assessed over the time by HPLC.

Due to the acid catalysed dissociation of the complex, we verified that, as expected, the integral areas of the peaks A, B, C, and D decreased, whereas new signals were formed and grew, corresponding to free ligands (m/z: 597.24). Interestingly, however, we found out that the rate of decrease of the areas of the signals A, B, C and D were not equal to each other; for instance, the decrease of the areas of the peaks A and B was significantly faster than that of the peaks C and D.

The decrease of the integral area values of signals of A, B, C, and D was thus assessed and plotted as a function of the time. The obtained results are graphically shown in FIG. 7 that highlights the observed differences existing among the behaviours of the four peaks.

$k_X$ pseudo-first-order rate constants (where $k_X$ is $=k_A$, $k_B$, $k_C$ and $k_D$ respectively), characterizing the dissociation rate of the different enantiomer pairs of the Gd(PCTA-tris-glutaric acid) complex and half-lives ($t_{1/2} = \ln2/k_X$) were then calculated by fitting the area —time data pairs, as explained in details in Example 7. The average half-life value for the isomeric mixture of Gd(PCTA-tris-glutaric acid) was also obtained, by considering the percentage composition of the mixture. Obtained results are summarized in Table 2, and compared with corresponding values referred in the literature for some reference contrast agents e.g. Gd-DOTA (Dotarem™) and Eu(PCTA) (europium complex of the 3,6,9,15-tetraazabicyclo[9.3.1]pentadeca-1(15),11,13-triene-3,6,9,-triacetic acid).

These results confirm that the dissociation rates of the four enantiomers pairs differ considerably among each other.

In particular, the enantiomers pair related to peak C has, unexpectedly, the highest kinetic inertness and lower tendency to release Gd among all other possible isomers.

In fact, the $t_{1/2}$ value measured for this pair of enantiomers C is, for example, about 68 times higher than the value e.g. of B. Besides, the $t_{1/2}$ value of the enantiomers pair related to the peak C is significantly higher than that measured for Eu(PCTA), equally having q=2, (see for instance Tircso, G. et al. Inorg Chem 2006, 45 (23), 9269-80) and is fully comparable with the $t_{1/2}$ value reported in the literature e.g. for Gd-DOTA (Dotarem™), which is the marketed contrast agents having best stability and inertness.

Figure 2:
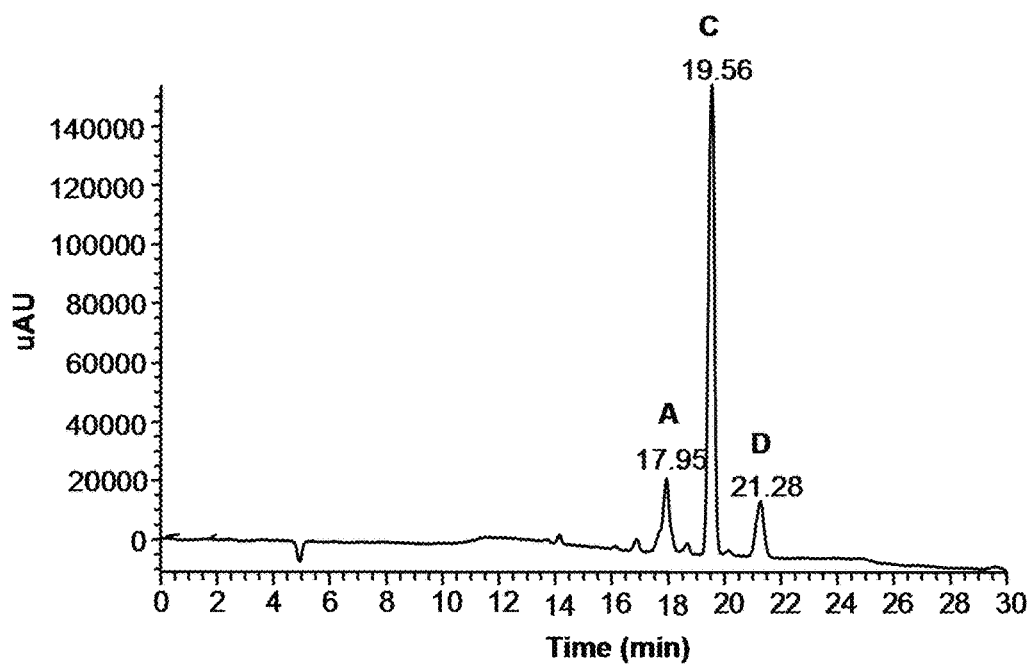
FIG. 2 shows a HPLC chromatogram of the RRR/SSS enantiomers pair C of the Gd(PCTA-tris-glutaric acid) obtained from Example 3.

Fractions enriched of this compound were then collected by flash chromatography e.g. as explained in detail in Example 3, leading to achieve the enantiomers pair related to the peak C with a purity degree of at least about 90% (as HPLC area %, see FIG. 2).

Surprisingly, a relaxivity value $r_1 = 9.3 \pm 0.1$ mM⁻¹s⁻¹ was obtained for the collected enantiomer pair, which is significantly higher than the $r_1$ value=7.2 recorded (under same conditions) for the isomeric mixture of Gd(PCTA-tris-glutaric acid) in EP1931673B1.

The unexpected combined higher relaxivity and higher inertness (resulting in higher tolerability) shown by this enantiomers pair are of particular interest.

Efforts have thus been spent in order to identify the couple of enantiomers related to the peak C.

Figure 4:
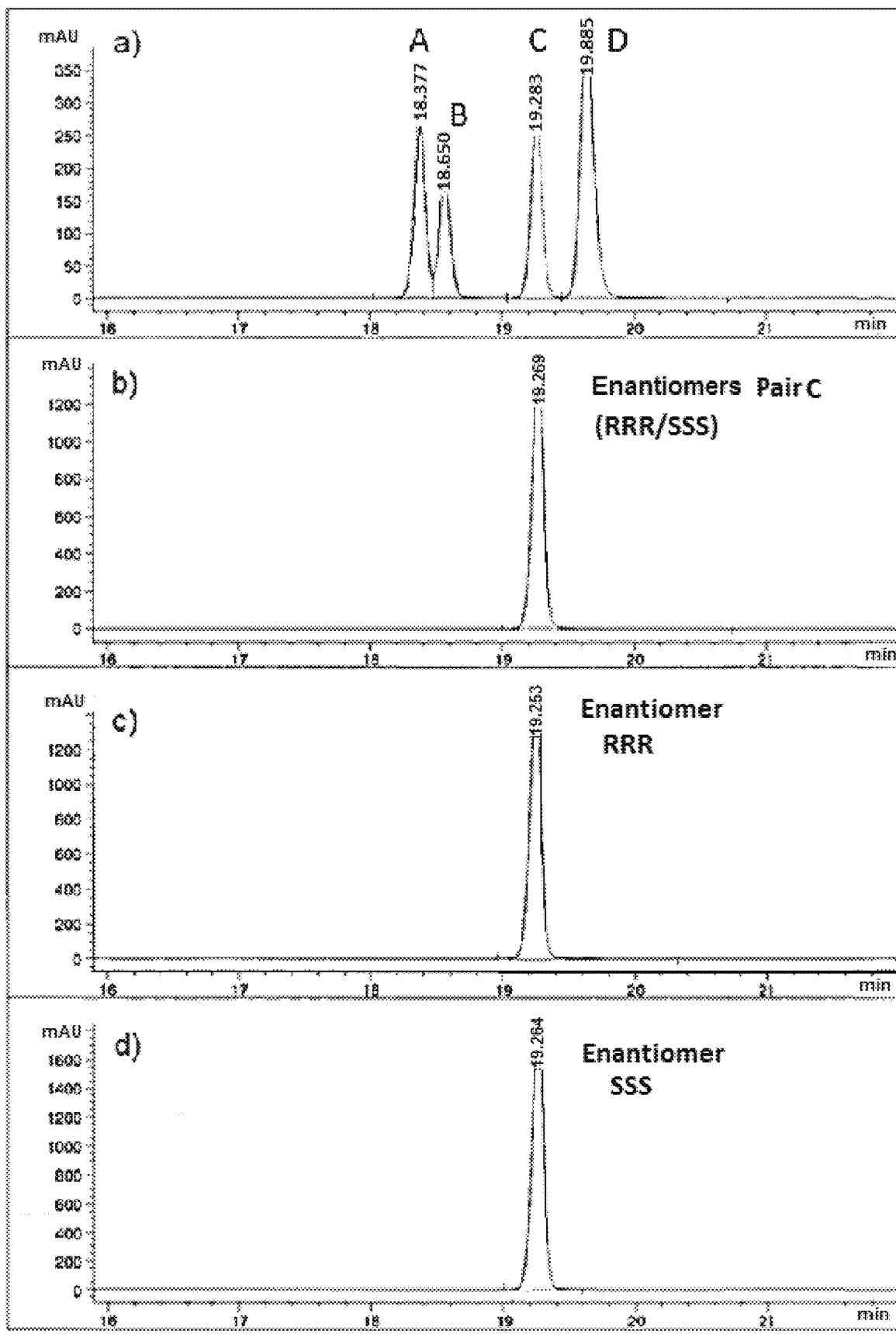
FIG. 4 shows the HPLC chromatograms of: a) isomeric mixture of Gd(PCTA-tris-glutaric acid) of Example 1; b) enantiomers pair C (compound VI of Example 3); c) RRR enantiomer (compound XII of Example 5), and d) SSS enantiomer (Compound XVII of Example 6).

In particular, a stereoselective synthesis of the RRR and SSS isomers of the Gd(PCTA-tris-glutaric acid), described in Example 5 and 6 respectively, has been set up, leading to achieve a crude with a major compound having the same HPLC retention time tr of peak C with normal reverse phase HPLC. By using the related isomer (R)-(−)-5-oxotetrahydrofuran-2-carboxylic acid as key intermediate, the corresponding SSS isomer of the Gd(PCTA-tris-glutaric acid) was also obtained, having same HPLC retention time (FIG. 4).

Instead, the synthesis of Gd(PCTA-tris-glutaric acid) carried out by using methyl (2S)-Bromoglutarate allows to achieve the complex as an isomeric mixture substantially indistinguishable from that collected with racemic methyl bromoglutarate, as disclosed by the prior art.

Figure 5:
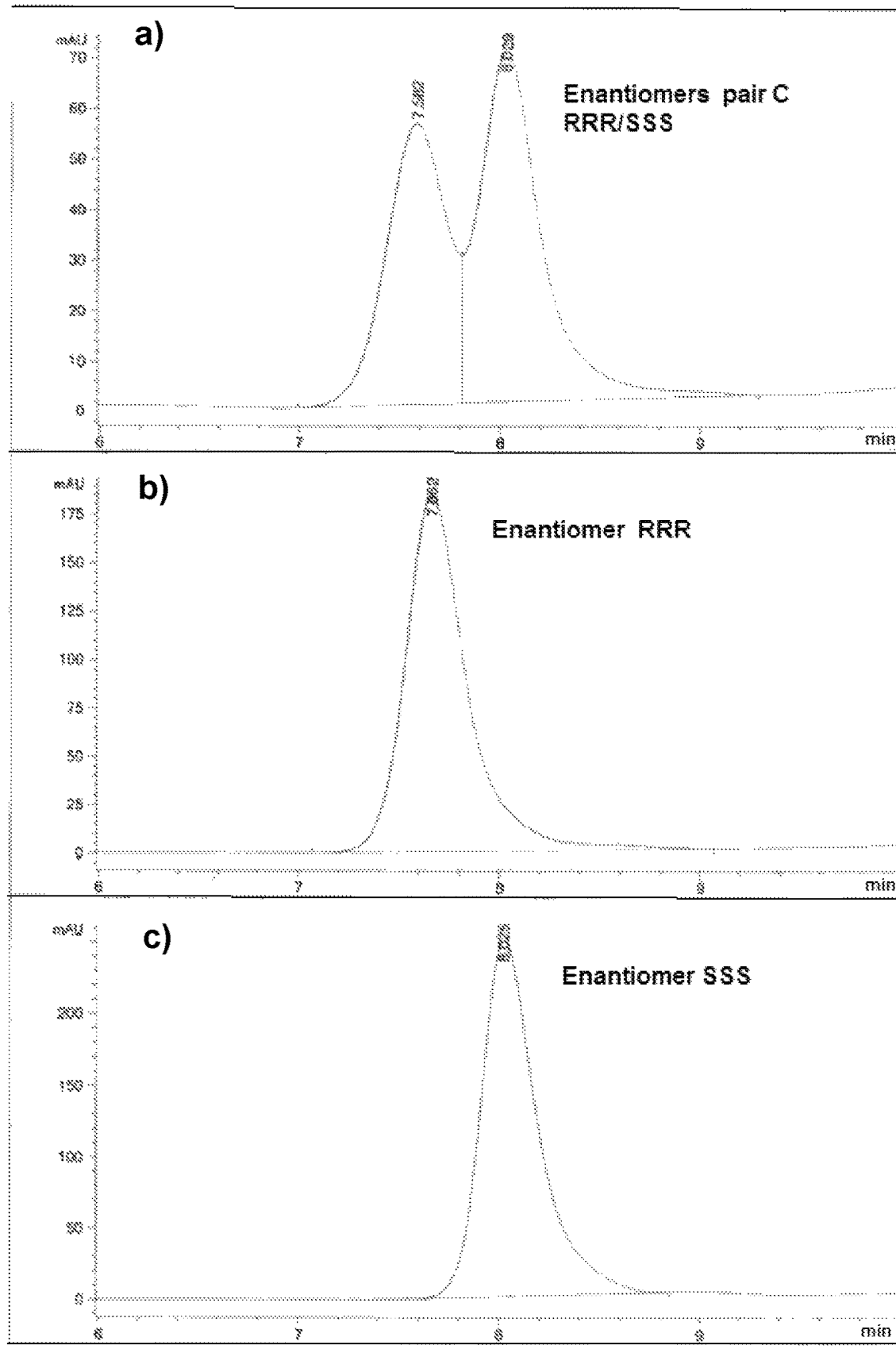
FIG. 5 shows the chiral HPLC chromatograms of: a) enantiomers pair C (Compound VI of Example 3), b) RRR enantiomer (compound XII of Example 5), and c) SSS enantiomer (Compound XVII of Example 6) of the Gd(PCTA-tris-glutaric acid).

The enantiomers pair related to the peak C was then analysed with a specific chiral HPLC method (allowing to separate the single enantiomers of the pair) by comparison with the synthesized SSS and RRR isomers of the Gd(PCTA-tris-glutaric acid). The obtained chromatograms, illustrated in FIG. 5, confirm that the two enantiomers related to the peak C have same retention times of the synthetized RRR and SSS isomers of the Gd(PCTA-tris-glutaric acid).

Moreover, crystals were formed from the enantiomers pair C with guanidinium oxalate as disclosed in detail in Example 10. An X-ray diffraction study of single crystals allowed to establish the RRR configuration of the chiral centres of the glutaric arms of the molecule, appreciable in FIG. 9, and the presence of an equimolar ratio of RRR and SSS isomers in each unit cell of the crystal, and, hence, the RRR/SSS racemic nature of the pair (FIG. 10).

These results all concur to establish that the compound associated with the peak C in fact consists of the RRR/SSS enantiomeric pair of Gd(PCTA-tris-glutaric acid), or RRR/SSS Gd(PCTA-tris-glutaric acid) as herein used interchangeably.

More particularly, the above results allowed to define that the compound corresponding to the peak C identified by the present invention comprises a mixture of [(αR,α'R,α"R)-α,α',α"-tris(2-carboxyethyl)-3,6,9,15-tetraazabicyclo[9.3.1]pentadeca-1(15),11,13-triene-3,6,9-triacetato(3-)-κN3,κN6,κN9,κN15,κO3,κO6,κO9]-gadolinium, or RRR-Gd(PCTA-tris-glutaric acid), of formula

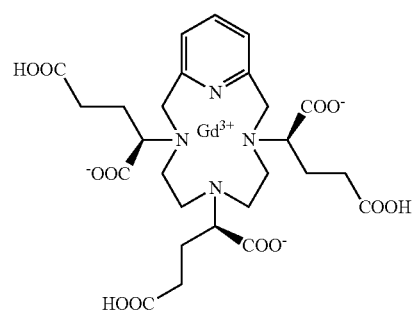

and the respective mirror isomer [(αS,α'S,α"S)-α,α',α"-tris(2-carboxyethyl)-3,6,9,15-tetraazabicyclo[9.3.1]pentadeca- 1(15),11,13-triene-3,6,9-triacetato(3-)-κN3,κN6,κN9, κN15,κO3,κO6,κO9]-gadolinium, or SSS-Gd(PCTA-tris-glutaric acid), of formula

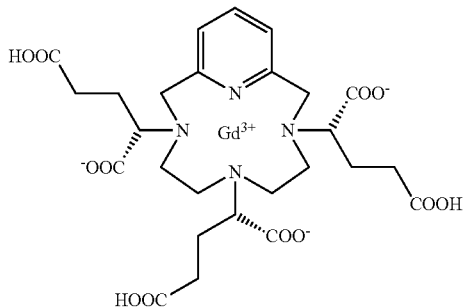

where said mixture is otherwise represented by the following formula Ic

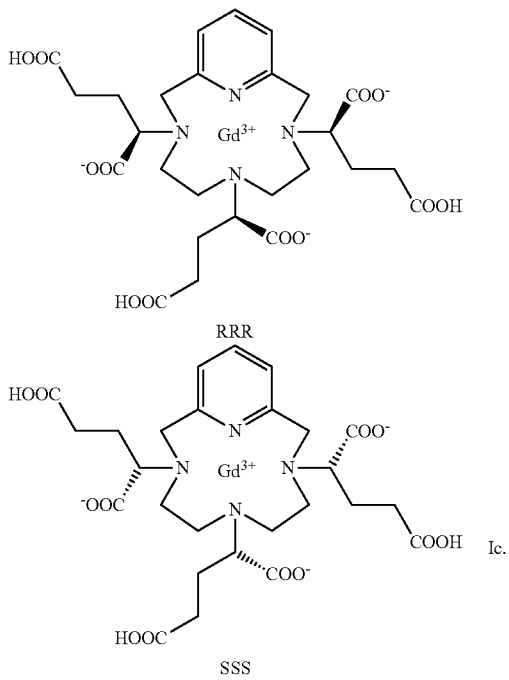

An aspect of the invention is thus the RRR/SSS pair of enantiomers of the of Gd(PCTA-tris-glutaric acid), the single enantiomers of the pair, their mixtures, the pharmaceutically acceptable salts thereof, their amide derivatives, and compositions comprising the same.

In particular, an embodiment of the invention relates to a compound which is preferably selected from the group consisting of: the individual enantiomer [(αR,α'R,α"R)-α, α',α"-tris(2-carboxyethyl)-3,6,9,15-tetraazabicyclo[9.3.1] pentadeca-1(15),11,13-triene-3,6,9-triacetato(3-)-κN3,κN6, κN9,κN15,κO3,κO6,κO9]-gadolinium (RRR enantiomer); its respective mirror isomer, namely the individual enantiomer [(αS,α'S,α"S)-α,α',α"-tris(2-carboxyethyl)-3,6,9, 15-tetraazabicyclo[9.3.1]pentadeca-1(15),11,13-triene-3,6, 9-triacetato(3-)-κN3,κN6,κN9,κN15,κO3,κO6,κO9]-gadolinium (SSS enantiomer); the RRR/SSS enantiomers pair thereof; and a pharmaceutically acceptable salt thereof.

According to a preferred embodiment the invention relates to the RRR/SSS enantiomers pair of the Gd(PCTA-tris-glutaric acid), otherwise herein more simply identified as "RRR/SSS Gd(PCTA-tris-glutaric acid)", comprising a mixture of the two individual RRR and SSS enantiomers of the complex, e.g., according to one embodiment of the invention, a racemic mixture thereof, or a salt thereof.

Another aspect of the invention relates to Gd(PCTA-tris-glutaric acid) enriched in any of above enantiomers, or mixtures thereof.

The expression "enriched" used with reference to an isomer, or enantiomer, or enantiomers pair according to the invention, (particularly when referred to Gd(PCTA-tris-glutaric acid) or amide derivatives thereof), includes within its meaning a mixture of isomers where such isomer, enantiomer, or enantiomers pair is present in a higher amount with respect to the amount typically contained in a mixture obtained according to a non-stereoselective synthetic procedure of the prior art.

Such enrichment (referred to an isomer, or enantiomers pair of Gd(PCTA-tris-glutaric acid)) corresponds to e.g. an amount of at least 50% of such isomer or enantiomers pair in the mixture, preferably at least 60%, more preferably at least 70%, and even more preferably at least 80%, e.g. of at least 90%.

In particular, another aspect of the invention relates to an isomeric mixture of Gd(PCTA-tris-glutaric acid) comprising at least 50% (relative to the isomeric composition thereof, i.e. to the sum of the individual isomers constituting the isomeric mixture of the Gd(PCTA-tris-glutaric acid)) of any of above isomers, i.e. where at least 50% of the isomeric mixture of the Gd(PCTA-tris-glutaric acid) complex consists of the RRR isomer [(αR,α'R,α"R)-α,α',α"-tris(2-carboxyethyl)-3,6,9,15-tetraazabicyclo[9.3.1]pentadeca-1(15),11, 13-triene-3,6,9-triacetato(3-)-κN3,κN6,κN9,κN15,κO3, κO6,κO9]-gadolinium; or the SSS isomer [(αS,α'S,α"S)-α, α',α"-tris(2-carboxyethyl)-3,6,9,15-tetraazabicyclo[9.3.1] pentadeca-1(15),11,13-triene-3,6,9-triacetato(3-)-κN3,κN6, κN9,κN15,κO3,κO6,κO9]-gadolinium; or a mixture thereof; or a salt thereof (the remaining amount of the complex being represented by an indiscriminate mixture of any others possible isomers thereof).

An embodiment of the invention thus relates to Gd(PCTA-tris-glutaric acid), or a salt thereof, where the respective enantiomer RRR, or enantiomer SSS or RRR/SSS mixture of these enantiomers represents at least 50% (e.g. by moles) of the isomeric mixture constituting said acid or salt.

Preferably, the enrichment of the Gd(PCTA-tris-glutaric acid) (in one of the above enantiomers or mixtures thereof) is of at least 60%, more preferably of at least 70%, most preferably of at least 80% e.g. of at least 90%.

More preferably the enrichment is in the RRR/SSS enantiomeric pair of the Gd(PCTA-tris-glutaric acid).

In a preferred embodiment the invention relates to the RRR/SSS enantiomers pair of the Gd(PCTA-tris-glutaric acid), or to an isomeric mixture of Gd(PCTA-tris-glutaric acid) comprising at least 50% of its RRR/SSS enantiomers pair, that is, in other words, a Gd(PCTA-tris-glutaric acid) where at least 50% of the complex consists of the RRR/SSS enantiomers pair thereof.

The RRR isomer [(αR,α'R,α"R)-α,α',α"-tris(2-carboxyethyl)-3,6,9,15-tetraazabicyclo[9.3.1]pentadeca-1(15),11, 13-triene-3,6,9-triacetato(3-)-κN3,κN6,κN9,κN15,κO3, κO6,κO9]-gadolinium, or a Gd(PCTA-tris-glutaric acid) enriched in this isomer can be prepared e.g. by use of a stereoselective synthesis that comprises alkylating 3,6,9,15-tetraazabicyclo[9.3.1]pentadeca-1(15),11,13-triene, or "pyclen" as herein used interchangeably, with (2S)-2-[(trifluoromethylsulfonyl)oxy]pentanedioic acid dimethyl ester, as described in better details in Example 5.

Likewise, the alternative use of (2R)-2-[(trifluoromethyl-sulfonyl)oxy]pentanedioic acid dimethyl ester (e.g. described in Example 6) allows to achieve the respective SSS isomer of the Gd(PCTA-tris-glutaric acid), or a Gd(PCTA-tris-glutaric acid) suitably enriched of the same.

The stereoselective syntheses of the RRR and SSS isomers of the Gd(PCTA-tris-glutaric acid) are new, and constitute a further embodiment of the present invention.

In another embodiment the invention relates to the above enantiomers, enantiomers pair, or enriched Gd(PCTA-tris-glutaric acid) in the form of a pharmaceutically acceptable salt thereof for use as contrast agents particularly suitable for Magnetic Resonance Imaging (MRI) analysis.

More particularly, a further embodiment of the invention relates to a pharmaceutically acceptable salt of a compound selected from an individual enantiomer RRR, or individual enantiomer SSS, or RRR/SSS enantiomers pair of the Gd(PCTA-tris-glutaric acid), or Gd(PCTA-tris-glutaric acid) at least 50% enriched in one of these individual enantiomers or, preferably, RRR/SSS enantiomers mixtures for use as a contrast agent, particularly suitable for Magnetic Resonance Imaging (MRI) analysis.

Suitable examples of pharmaceutically acceptable salts for instance include the salts with a cation of an inorganic base selected from an alkali or alkaline-earth metal such as potassium, sodium, calcium or magnesium, or of an organic base selected from ethanolamine, diethanolamine, morpholine, glucamine, N-methylglucamine, N,N-dimethylglucamine or of an amino acid selected from lysine, arginine and ornithine.

According to another aspect, the invention relates to a conjugate of one of the above compound or isomeric mixtures, preferably with an amine of formula $NHR_1R_2$.

An embodiment of the invention relates to an amide derivative of the RRR enantiomer, SSS enantiomer, or a mixture of such two enantiomers of Gd(PCTA-tris-glutaric acid), of formula (II A)

$F(NR_1R_2)_3$                      (II A).

Another embodiment the invention refers to an isomeric mixture of an amide derivative of Gd(PCTA-tris-glutaric acid) comprising at least 50% of the individual enantiomer RRR, or enantiomer SSS, or of a mixture of these enantiomers, of formula (II B)

$F'(NR_1R_2)_3$                      (II B).

In the formulas (II A) and (II B) referred to above, the meanings of F, F', $R_1$ and $R_2$ are as formerly defined.

Preferred examples include amide derivatives of the above formula (II A) in which F is a mixture of RRR and SSS enantiomers residues (or pair of RRR/SSS enantiomers residues) of Gd(PCTA-tris-glutaric acid), or of the above formula (II B) in which F' is an isomeric mixture of Gd(PCTA-tris-glutaric acid) residue comprising at least 50% of a mixture of RRR and SSS enantiomers residues.

In a preferred embodiment the invention relates to an amide derivative of the above formula (II B) where F' is an isomeric mixture of a Gd(PCTA-tris-glutaric acid) residue of the above formula III comprising at least 50% of a mixture of RRR and SSS enantiomers residues, respectively of formula (IIIA) and (IIIB).

Preferably, in these amide derivatives, F' is at least 60% enriched (i.e. comprises at least 60% of), more preferably at least 70%, most preferably at least 80%, e.g. particularly preferably at least 90% enriched in the mixture of RRR and SSS enantiomer residues. Suitable examples include amide derivatives of the above formula (II B) in which $R_1$ is H and $R_2$ is a $C_1$-$C_3$ alkyl substituted by one or more, preferably one or two, and, more preferably two hydroxyl groups.

In a preferred embodiment, the invention relates to an isomeric mixture of amide derivatives of the above formula (II B) where F' is a residue of formula (III) as above defined, $R_1$ is H, and $R_2$ is $C_1$-$C_3$ alkyl substituted by one or two hydroxyl groups. More preferably, $R_2$ is a serinol residue or, even more preferably, an isoserinol residues, e.g. selected from R isoserinol, S isoserinol or racemic isoserinol. Most preferably the amide compound is with racemic isoserinol.

Non-limiting, representative examples of above compounds for instance include:

[(αS,α'S,α"S)-α,α',α"-tris[3-[(2(S),3-dihydroxypropyl)amino]-3-oxopropyl]-3,6,9,15-tetraazabicyclo[9.3.1]pentadeca-1(15),11,13-triene-3,6,9-triacetato(3-)-κN3,κN6,κN9,κN15,κO3,κO6,κO9]-gadolinium, (or isomer SSS-SSS), of formula;

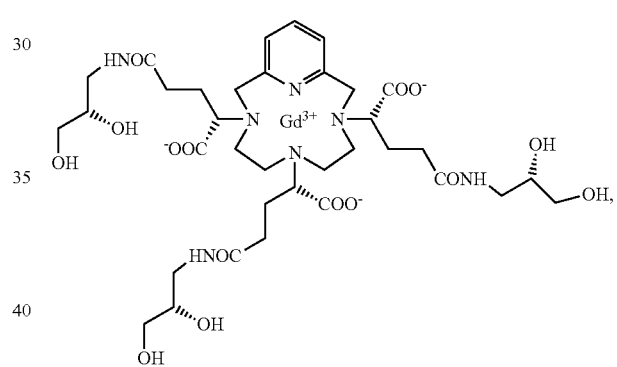

[(αR,α'R,α"R)-α,α',α"-tris[3-[(2(R),3-dihydroxypropyl)amino]-3-oxopropyl]-3,6,9,15-tetraazabicyclo[9.3.1]pentadeca-1(15),11,13-triene-3,6,9-triacetato(3-)-κN3,κN6,κN9,κN15,κO3,κO6,κO9]-gadolinium (or isomer RRR-RRR) of formula

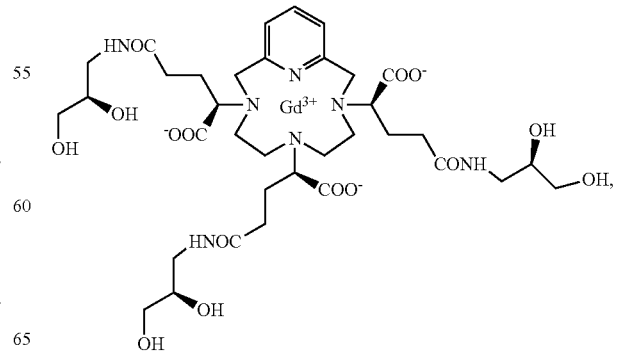

[(αR,α'R,α"R)-α,α',α"-tris[3-[(2(S),3-dihydroxypropyl)amino]-3-oxopropyl]-3,6,9,15-tetraazabicyclo[9.3.1]pentadeca-1(15),11,13-triene-3,6,9-triacetato(3-)-κN3,κN6,κN9,κN15,κO3,κO6,κO9]-gadolinium (or isomer RRR-SSS) of formula

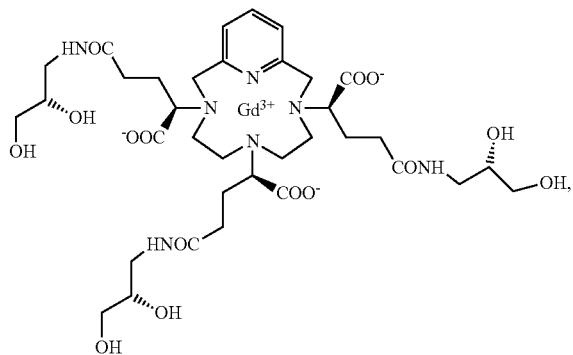

[(αS,α'S,α"S)-α,α',α"-tris[3-[(2(R),3-dihydroxypropyl)amino]-3-oxopropyl]-3,6,9,15-tetraazabicyclo[9.3.1]pentadeca-1(15),11,13-triene-3,6,9-triacetato(3-)-κN3,κN6,κN9,κN15,κO3,κO6,κO9]-gadolinium (or isomer SSS-RRR) of formula

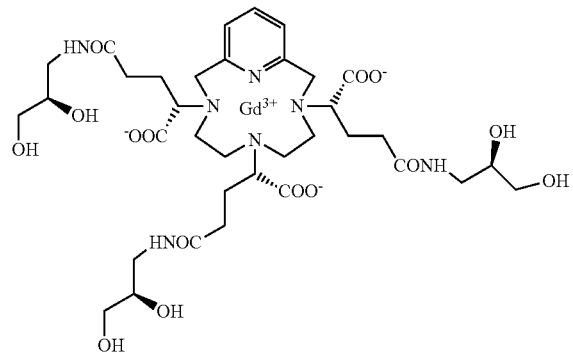

or respective isomers where the isoserinol moieties are in the RSR, SSR, SRS, RSS, or RRS, configurations.

Amides of the formula (II B) with isoserinol have the same molecular formula of Gadopiclenol but comprises a central moiety F' at least 50% enriched in the RRR isomer, or SSS isomer residue or, more preferably, in the mixture of RRR and SSS enantiomers residues of Gd(PCTA-tris-glutaric acid).

Figure 6:
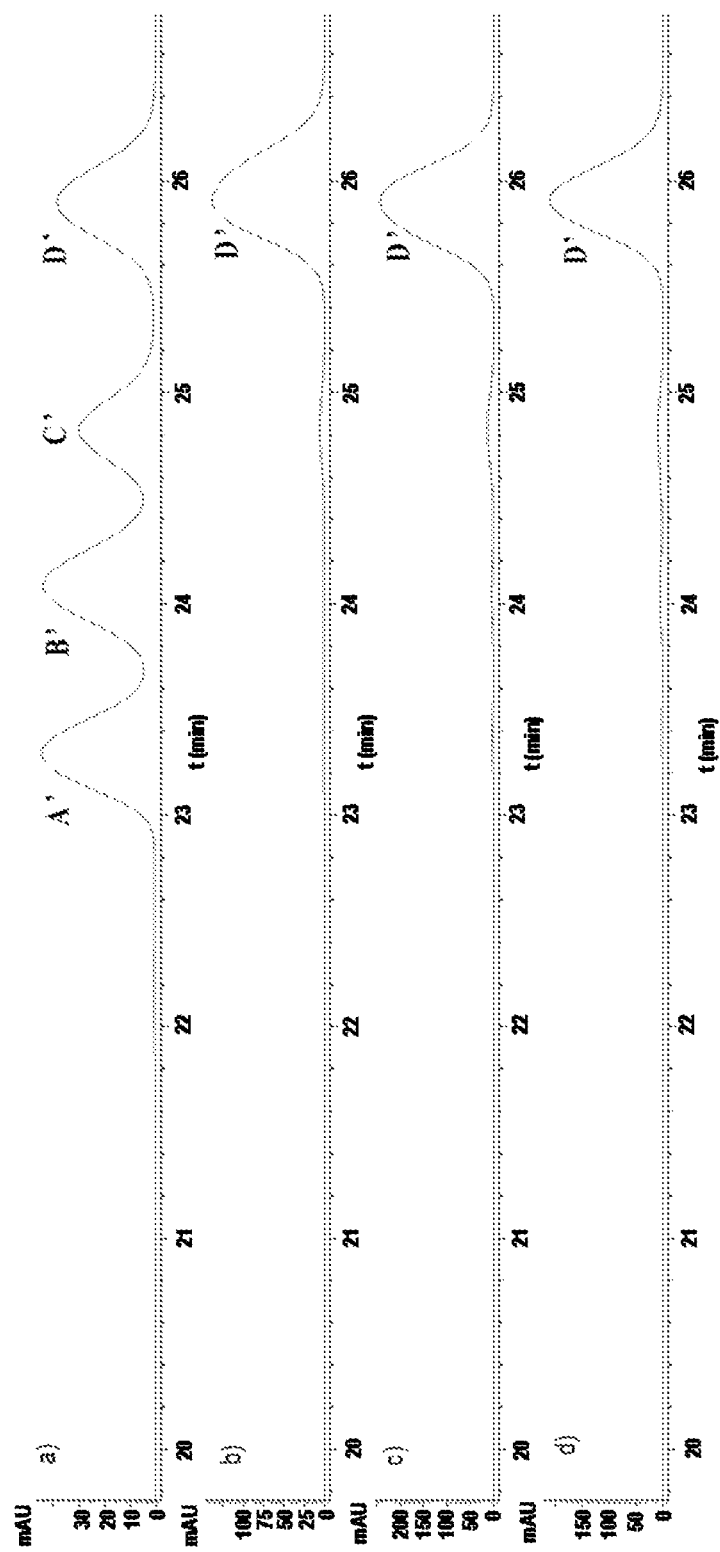
FIG. 6 shows the HPLC chromatograms of the amide derivatives obtained by reaction of Gd(PCTA-tri-glutaric acid) with isoserinol. a): amide derivative obtained as an isomeric mixture from Example 2, where the 4 major peaks are, for convenience, identified as A', B' C' and D'; b): amide derivative obtained by reaction of RRR/SSS Gd(PCTA-tris-glutaric acid) with R-isoserinol; c): amide derivative obtained by reaction of RRR/SSS Gd(PCTA-tris-glutaric acid) with S-isoserinol; and d): amide derivative obtained by reaction of RRR/SSS Gd(PCTA-tris-glutaric acid) with racemic isoserinol.

Notably, regardless of the type of isoserinol used, (i.e. whether it is a R or S isomer, or racemic isoserinol), its conjugation with the RRR/SSS enantiomers pair of Gd(PCTA-tris-glutaric acid) leads to conjugates that, as shown in FIG. 6, have the same retention time and are, therefore, indistinguishable by HPLC. FIG. 6 further shows that this retention time is the same of the peak D' separated by HPLC from Gadopiclenol obtained as an isomeric mixture in the Example 2.

Surprisingly, the improved properties of the RRR/SSS Gd(PCTA-tris-glutaric acid) are substantially maintained after its conjugation with isoserinol, regardless of the configuration of the coupled isoserinol.

In particular the isoserinol conjugation with RRR/SSS Gd(PCTA-tris-glutaric acid) leads to an amide derivative having same molecular formula but greater kinetic inertness and relaxivity of Gadopiclenol obtained as an isomeric mixture with the synthetic procedure of the prior art.

Indeed, the same test performed to assess the kinetic inertness of the four different enantiomer pairs separated from the isomeric mixture of Gd(PCTA-tris-glutaric acid) was repeated by using Gadopiclenol (isomeric mixture) as obtained in Example 2 and the amide derivatives obtained by conjugation of RRR/SSS Gd(PCTA-tris-glutaric acid) with i) R-isoserinol; ii)S-isoserinol; and iii) racemic isoserinol, respectively.

The average half-life of the obtained conjugated compounds and of Gadopiclenol (isomeric mixture) were calculated considering the decrease of the HPLC total area over time as described in detail in Example 8. For amide derivatives obtained by reaction of RRR/SSS Gd(PCTA-tris-glutaric acid) with i) R-isoserinol; ii)S-isoserinol; and iii) racemic isoserinol the $k_X$ pseudo-first-order rate constants and half-lives ($t_{1/2}$=ln $2/k_X$) were also calculated by fitting the area—time data pairs as carried out for RRR/SSS Gd(PCTA-tris-glutaric acid) in Example 7.

Obtained results are summarized in Table 3, and compared with corresponding values referred in the literature for some reference contrast agents e.g. Gd-DOTA (Dotarem™) and Eu(PCTA).

The data of Table 3 from one side display the very good agreement existing between $t_{1/2}$ values of complexes obtained by coupling RRR/SSS Gd(PCTA-tris-glutaric acid) with R, S and racemic-isoserinol estimated from the area values and calculated by the fitting of the area-time kinetic data.

On the other side, the data of Table 3 highlight that all the $t_{1/2}$ values of the amide compounds obtained by reaction of RRR/SSS Gd(PCTA-tris-glutaric acid) with i) R-isoserinol; ii)S-isoserinol; and iii) racemic isoserinol are about 8 times higher than that of Gadopiclenol (isomeric mixture), thereby confirming that higher kinetic inertness shown by RRR/SSS Gd(PCTA-tris-glutaric acid) is substantially maintained even after its coupling with isoserinol.

The total consistency of half-life values obtained for the different complex compounds resulting from the conjugation of RRR/SSS Gd(PCTA-tris-glutaric acid) with R, S or racemic isoserinol, indicates also that the chirality of the isoserinol pendant has no influence for the kinetic inertness of the final complex. The $r_1$ relaxivity was also measured for the compounds obtained by conjugation of RRR/SSS Gd(PCTA-tris-glutaric acid) with R, S and racemic isoserinol, under same conditions used in the literature for Gadopiclenol.

Obtained results are compared in Table 5. Again, regardless of the configuration of the appended isoserinol, the $r_1$ relaxivity measured both in water and in HSA for conjugated compounds obtained from RRR/SSS Gd(PCTA-tris-glutaric acid) is higher than that reported in the relevant art for Gadopiclenol.

An amide derivative is thus obtained by conjugation of the RRR/SSS Gd(PCTA-tris-glutaric acid) of the present invention with isoserinol that, despite having the same structure of the Gadopiclenol compound, is characterized by an improved kinetic inertness and higher relaxivity.

Crystals were then obtained from the amide derivative resulting from the conjugation of the RRR/SSS Gd(PCTA-tris-glutaric acid) with racemic isoserinol as described in detail in Example 10. An X-ray diffraction study of a single crystal obtained from a ternary complex formed between carbonate anion and the amide derivative confirmed the RRR/SSS configuration of the glutaric arms of the core molecule C.

Figure 11:
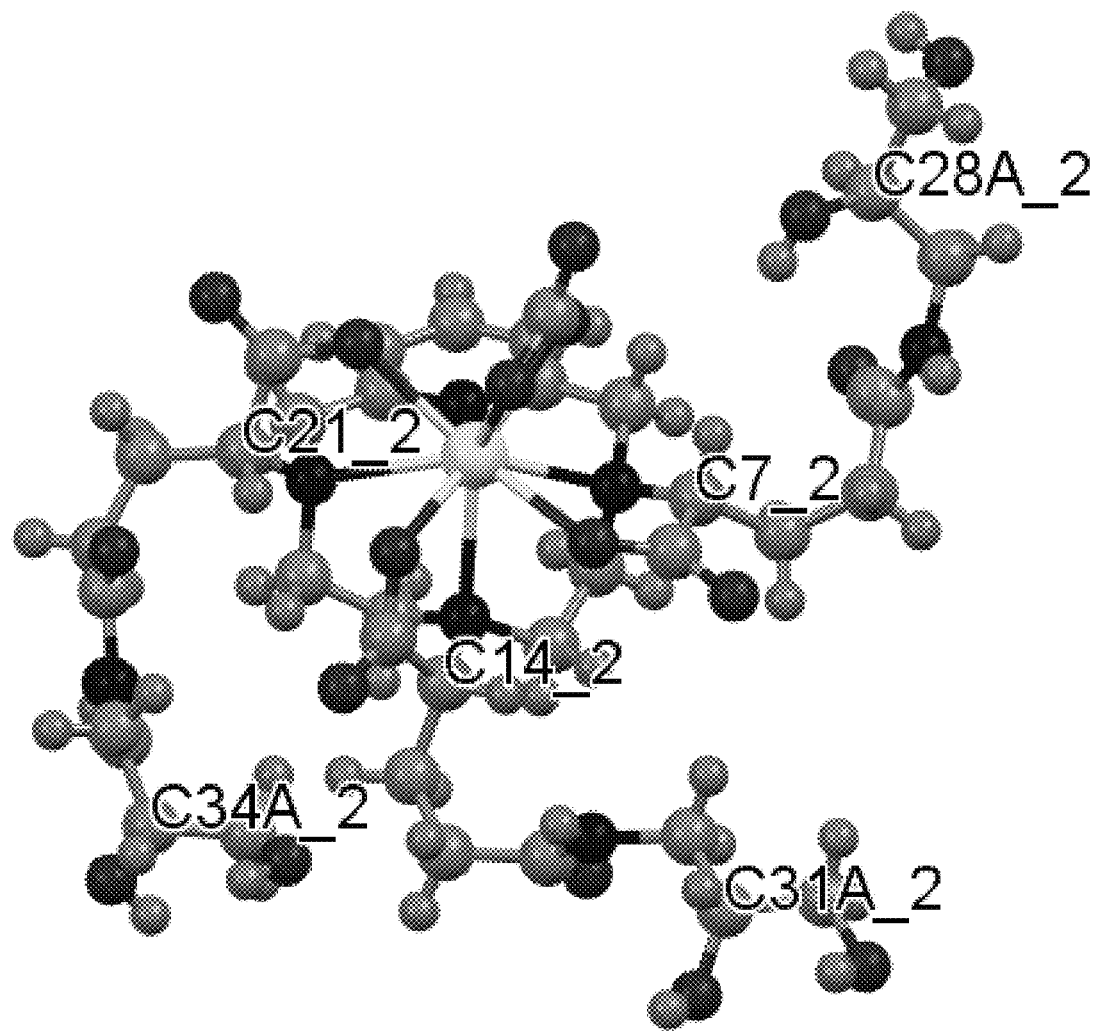
FIG. 11 shows the X-ray structure of a single crystal obtained from a ternary complex formed between carbonate anion and the amide compound D' obtained by coupling reaction of RRR/SSS Gd(PCTA-tris-glutaric acid) with racemic isoserinol, and statistical analysis of the collected crystals.

The X-ray structure, and a statistical analysis of all collected crystals are provided in FIG. 11.

The results of the stereoselective synthesis of the individual RRR or SSS isomer, and the (crystal) structures recorded from both the enantiomers pair C and the conjugate thereof with isoserinol are thus all consistent with each other, and allow to establish that the compound attributed to the peak C in the HPLC of FIG. 1 corresponds in fact to the RRR/SSS enantiomers pair of Gd(PCTA-tris-glutaric acid).

The synthesis of the RRR and SSS isomers of the Gd(PCTA-tris-glutaric acid) represents a further embodiment of the invention.

In particular, another embodiment of the invention relates to a stereoselective process for the preparation of Gd(PCTA-tris-glutaric acid) enriched in the isomer [(αR,α'R,α"R)-α, α',α"-tris(2-carboxyethyl)-3,6,9,15-tetraazabicyclo[9.3.1] pentadeca-1(15),11,13-triene-3,6,9-triacetato(3-)-κN3,κN6, κN9,κN15,κO3,κO6,κO9]-gadolinium (RRR isomer), that comprises a) obtaining (2S)-2-[(trifluoromethylsulfonyl)oxy]pentanedioic acid dimethyl ester, of formula

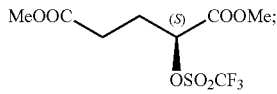

and b) alkylating 3,6,9,15-tetraazabicyclo[9.3.1]pentadeca-1 (15),11,13-triene of formula

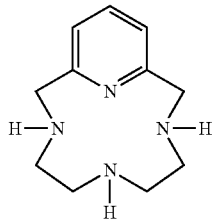

with the collected (2S)-2-[(trifluoromethylsulfonyl)oxy] pentanedioic acid dimethyl ester.

In one embodiment the process allows to obtain Gd(PCTA-tris-glutaric acid) at least 55% enriched, preferably at least 60%, more preferably at least 70%, and most preferably at least 80% e.g. about 85% enriched in the desired RRR isomer of the complex.

Similarly, the alternative use of (2R)-2-[(trifluoromethylsulfonyl)oxy]pentanedioic acid dimethyl ester in step a) of the process allows to achieve the respective SSS isomer of the Gd(PCTA-tris-glutaric acid), or a Gd(PCTA-tris-glutaric acid) suitably enriched in this isomer.

In a still further embodiment the invention relates to the RRR/SSS pair of enantiomers of the Gd(PCTA-tris-glutaric acid) or a Gd(PCTA-tris-glutaric acid) at least 50% enriched with this same enantiomeric pair for use as intermediate in the preparation of a derivative thereof such as, preferably, an amide derivative.

A still further embodiment of the invention relates to a process for the synthetic preparation of an amide derivative of Gd(PCTA-tris-glutaric acid) of formula (II A)

$$F(NR_1R_2)_3 \qquad (II\ A)$$

where F, $R_1$ and $R_2$ are as above said, which comprises:
a) obtaining the RRR, or the SSS isomer of the Gd(PCTA-tris-glutaric acid), or a mixture thereof; and
b) converting the isomer, or mixture of isomers, obtained from step a) in the desired amide derivative.

The step a) of this process, leading to achieve the RRR, or the SSS isomer of the Gd(PCTA-tris-glutaric acid) is for instance carried out as above said and as provided in detail, for instance in Examples 5 and 6.

On the other side, the step b) of the process can be carried out according to conventional procedures, for instance reported in the above quoted prior art.

A further aspect of the invention relates to a process for the synthetic preparation of an isomeric mixture of an amide derivatives of Gd(PCTA-tris-glutaric acid) of the above formula (II B)

$$F(NR_1R_2)_3 \qquad (II\ B)$$

where F', $R_1$ and $R_2$ are as above said, which comprises:
a') obtaining an isomeric mixture of the Gd(PCTA-tris-glutaric acid) comprising at least 50% of the respective enantiomer RRR, or SSS, or, preferably, of a mixture thereof; and
b') converting the isomeric mixture of the Gd(PCTA-tris-glutaric acid) obtained from step a') in the corresponding isomeric mixture of amide derivative of interest.

The step a') of this process, e.g. leading to achieve the isomeric mixture of Gd(PCTA-tris-glutaric acid) comprising at least 50% of the RRR/SSS enantiomers pair of the same, can for example be obtained by chromatography, including preparative HPLC or flash chromatography, stating from the Gd(PCTA-tris-glutaric acid) obtained as an isomeric mixture with known procedures, for instance as disclosed in Example 3.

On the other side, the step b') of the process, consisting of coupling the enriched isomeric mixture of Gd(PCTA-tris-glutaric acid) collected from step a') with the amine of interest can be carried out according to conventional procedures, for instance reported in the above quoted prior art.

For instance, the product recovered from step a') may be reacted with isoserinol, e.g. by using the synthetic procedure provided in detail in Example 4.

An additional embodiment of the invention relates to an amide of above formula (II A) or (II B) for use as contrast agents, particularly suitable for Magnetic Resonance Imaging (MRI) analysis.

In particular, in another embodiment the invention relates to a compound selected from the group consisting of: the individual RRR or SSS enantiomers, a mixture of such RRR/SSS enantiomers of the Gd(PCTA-tris-glutaric acid), an isomeric mixture of Gd(PCTA-tris-glutaric acid) at least 50% enriched in one of such individual RRR or SSS enantiomers or in a mixture thereof, a pharmaceutically acceptable salts thereof, an amide derivative thereof of formula (II A) or (II B), for the preparation of a pharmaceutical formulation for use in the diagnostic imaging, either in vivo or in vitro, ex vivo, of a human or animal body organ, tissue or region or of a biological sample, including cells, biological fluids and biological tissues originating from a live mammal patient, and preferably, human patient, by use of the MRI technique.

A further aspect of the invention concerns a pharmaceutical composition for diagnostic use comprising at least one of the above isomeric compound or isomeric mixture according to the invention, or a pharmaceutically acceptable salt or amide derivative thereof as above said, in admixture with one or more physiologically acceptable excipients, diluents or solvents.

Preferably, the pharmaceutical composition comprises an amide derivative of the above formula (II A) in which, in said formula (II A):
F is the residue of the RRR/SSS enantiomers pair of the Gd(PCTA-tris-glutaric acid);
or, more preferably, an isomeric mixture of an amide derivative of the above formula (II B) in which, in the formula (II B) F' is an isomeric mixture of Gd(PCTA-tris-glutaric acid) at least 50% enriched of said RRR/SSS enantiomer pair, and —$NR_1R_2$ is the isoserinol residue.

In a preferred embodiment, the pharmaceutical composition comprises an amide compound according to the formula (II B) in which F' is the residue of a Gd(PCTA-tris-glutaric acid) at least 60%, preferably at least 70%, more preferably at least 80% enriched, e.g. most preferably at least 90% enriched in the RRR/SSS enantiomers pair of the Gd(PCTA-tris-glutaric acid), conjugated with isoserinol of formula

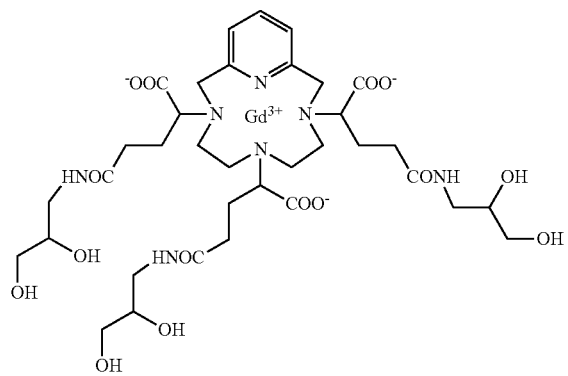

In an additional aspect the invention relates to a MRI contrast medium comprising an effective amount of at least one isomeric compound or isomeric mixture according to the invention, as above said, or of a pharmaceutical acceptable salt thereof, or amide derivative thereof in combination with one or more pharmaceutically acceptable excipients, diluents or solvents.

To this extent, and unless otherwise provided, the term "effective amount" or "effective dose", as used herein, refers to any amount of Gd(PCTA-tris-glutaric acid) according to the invention or pharmaceutically acceptable salt thereof, or amide derivative thereof of formula (II A) or (II B) or pharmaceutical composition thereof, that is sufficient to fulfil its intended diagnostic purpose(s): i.e., for example, to ex vivo visualize a biological element including cells, biological fluids and biological tissues or the in vivo diagnostic imaging of body organs, tissues or regions of a patient.

Unless otherwise indicated, the term "individual patient" or "patient" as used herein refers to a living human or animal patient, and, preferably a human being undergoing MR diagnostic assessment.

Details concerning dosages, dosage forms, modes of administration, pharmaceutically acceptable carriers, excipients, diluents, adjuvants and the like are known in the art.

Non-limiting examples of preferred compounds of the invention, procedure consenting their preparations, and their characterization is reported in the following section, aimed to illustrate the invention in greater detail without limiting its scope.

Experimental Part
HPLC Characterization of the Obtained Compounds.
General Procedures
Procedure 1: HPLC Characterization of Gd(PCTA-Tris-Glutaric Acid) (Isomeric Mixture and Individual/Enriched Isomers).

The HPLC characterization of the Gd(PCTA-tris-glutaric acid) obtained as isomeric mixture from Example 1 was performed with Agilent 1260 Infinity II system. The experimental setup of the HPLC measurements are summarized below.

| Analytical conditions | | | |
|---|---|---|---|
| HPLC system | HPLC equipped with quaternary pump, degasser, autosampler, PDA detector (Agilent 1260 Infinity II system) | | |
| Stationary phase: | Phenomenex Gemini ® 5 µm C18 110Å | | |
| Mobile phase: | $H_2O$/HCOOH 0.1%: Methanol | | |
| Elution: Gradient | Time (min) | $H_2O$/HCOOH 0.1% | Methanol |
| | 0 | 95 | 5 |
| | 5 | 95 | 5 |
| | 30 | 50 | 50 |
| | 35 | 50 | 50 |
| | 40 | 95 | 5 |
| Flow | 0.6 mL/min | | |
| Temperature | 25° C. | | |
| Detection | PDA scan wavelength 190-800 nm | | |
| Injection volume | 50 µL | | |
| Sample Conc. | 0.2 mM Gd(PCTA-tris-glutaric acid) complex | | |
| Stop time | 40 min | | |
| Retention time | GdL ≅ 18-21 min. | | |

Obtained HPLC chromatogram is shown in FIG. 1
The HPLC chromatogram of the enriched enantiomers pair C is shown in FIG. 2.

Procedure 2: HPLC Characterization of Gadopiclenol (Isomeric Mixture) and Compounds Obtained by Coupling of Enantiomers Pair C with R, S, or Racemic Isoserinol.

The HPLC characterization of Gadopiclenol either as isomeric mixture obtained from Example 2, or as the compound obtained by conjugation of enantiomers pair C of the Gd(PCTA-tris-glutaric acid) with R, S, or racemic isoserinol was performed with Thermo Finnigan LCQ DECA XPPlus system. The experimental setup of the HPLC measurements are summarized below.

| Analytical conditions | | | |
|---|---|---|---|
| HPLC system | HPLC equipped with quaternary pump, degasser, autosampler, PDA and MS detector (LCQ Deca XP-Plus-Thermo Finnigan) | | |
| Stationary phase: | Phenomenex Gemini 5u C18 110A | | |
| Mobile phase: | $H_2O$/TFA 0.1%: Acetonitrile/0.1% TFA | | |
| Elution: Gradient | Time (min) | $H_2O$/TFA 0.1% | Acetonitrile/ 0.1% TFA |
| | 0 | 100 | 0 |
| | 5 | 100 | 0 |

-continued

|  | 22 | 90 | 10 |
|---|---|---|---|
|  | 26 | 90 | 10 |
| Flow | 0.5 mL/min | | |
| Temperature | 25° C. | | |
| Detection | PDA scan wavelenght 190-800 nm | | |
|  | MS positive mode-Mass range 100-2000 | | |
| Injection volume | 50 μL | | |
| Sample conc. | 0.2 mM Gd complex | | |
| Stop time | 26 min | | |
| Retention time | GdL ≅ 20-22 min. | | |

Obtained HPLC chromatograms are shown in FIG. 6.

Procedure 3: Chiral HPLC Method for the Separation of Enantiomers of the Compound C A specific chiral HPLC method was set up in order to separate the RRR and SSS enantiomers of the enantiomers pair C (compound VI), prepared as described in Example 3. The separation and characterization of the enantiomers were performed with Agilent 1200 system or Waters Alliance 2695 system. The experimental setup of the HPLC measurements are summarized below.

| Analytical conditions | |
|---|---|
| HPLC System | HPLC equipped with quaternary pump, degasser, autosampler, PDA detector |
| Stationary phase | SUPELCO Astec CHIROBIOTIC 5 μm 4.6 × 250 mm |
| Mobile phase | H$_2$O/HCOOH 0.025%: Acetonitrile |
| Elution : | isocratic 2% Acetonitrile for 30 minutes |
| Flow | 1 mL/min |
| Column Temperature | 40° C. |
| Detection | 210-270 nm. |

Obtained HPLC chromatogram is shown in FIG. 5*a*) compared to the chromatograms of the pure RRR enantiomer (compound XII of Example 5, Tr. 7.5 min.) and the pure SSS enantiomer (Compound XVII of Example 6, Tr. 8.0 min), shown in FIG. 5*b*) and 5*c*), respectively.

Example 1: Synthesis of Gd(PCTA-Tris-Glutaric Acid) (Isomeric Mixture)

Gd(PCTA-tris-glutaric acid) as an indiscriminate mixture of stereoisomers has been prepared by using the procedure reported in above mentioned prior-art, according to the following synthetic Scheme 1:

Scheme 1

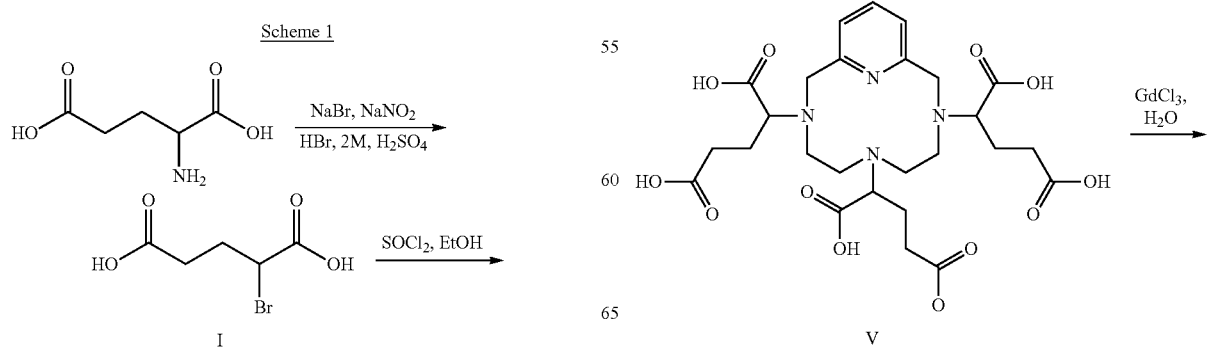

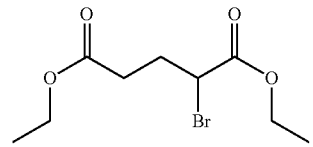

II

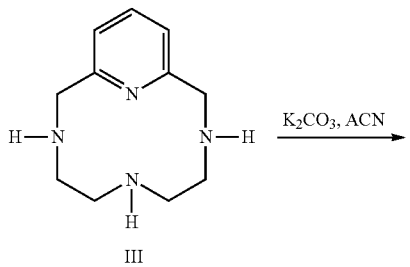

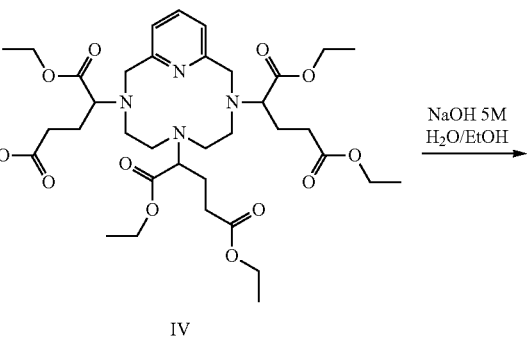

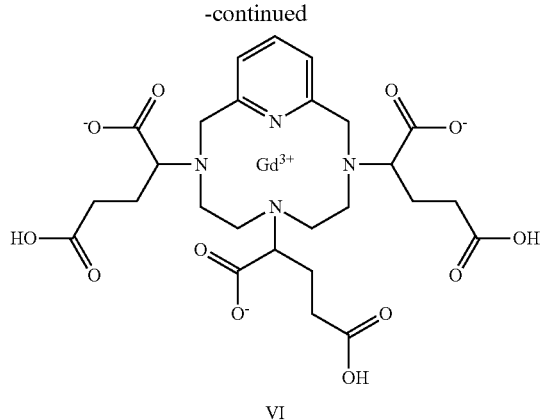

VI a) Preparation of Compound II

Racemic glutamic acid (33.0 g, 0.224 mol) and sodium bromide (79.7 g, 0.782 mol) were suspended in 2M HBr (225 mL). The suspension was cooled to −5° C. and $NaNO_2$ (28.0 g, 0.403 mol) was slowly added in small portions over 2.5 hours, maintaining the inner temperature lower than 0° C. The yellow mixture was stirred for additional 20 minutes at a temperature of −5° C.; then concentrated sulfuric acid (29 mL) was dropped in the mixture. The obtained dark brown mixture was warmed to RT and then extracted with diethyl ether (4×150 mL). The combined organic phases were washed with brine, dried over $Na_2SO_4$ and concentrated to a brown oil (21.2 g), used in the following step without further purification. The oil was dissolved in ethanol (240 mL), the resulting solution was cooled in ice and thionyl chloride (14.5 mL, 0.199 mol) was slowly added. The slightly yellow solution was stirred at RT for 2 days. Then the solvent was removed in vacuum and the crude oil was dissolved in dichloromethane (200 mL) and washed with 5% aq. $NaHCO_3$(4×50 mL), water (1×50 mL) and brine (1×50 mL). The organic phase was concentrated and purified on silica eluting with petroleum ether-ethyl acetate 3:1, obtaining 19.5 g of pure product. (Yield 33%).

b) Preparation of Compound IV

A solution of Compound II (17.2 g, 0.0645 mol) in acetonitrile (40 mL) was added to a suspension of 3,6,9,15-tetraazabicyclo[9.3.1]pentadeca-1(15),11,13-triene (pyclen) Compound (III) (3.80 g, 0.018 mol) and $K_2CO_3$ (11.2 g, 0.0808 mol) in acetonitrile (150 mL). The yellow suspension was heated at 65° C. for 24 h, then the salts were filtered out and the organic solution was concentrated. The orange oil was dissolved in dichloromethane and the product was extracted with 1M HCl (4×50 mL). The aqueous phases were combined, cooled in ice and brought to pH 7-8 with 30% aq. NaOH. The product was then extracted with dichloromethane (4×50 mL) and concentrated to give a brown oil (10.1 g, yield 73%). The compound was used in the following step without further purification.

c) Preparation of Compound V

Compound IV (9.99 g, 0.013 mol) was dissolved in Ethanol (40 mL) and 5M NaOH (40 mL). The brown solution was heated at 80° C. for 23 h. Ethanol was concentrated; the solution was cooled in ice and brought to pH 2 with conc HCl. The ligand was purified on resin Amberlite XAD 1600, eluting with water-acetonitrile mixture, obtaining after freeze-drying 5.7 g as white solid (yield 73%). The product was characterized in HPLC by several peaks.

d) Preparation of Compound VI

Compound V (5.25 g, 0.0088 mol) was dissolved in deionized water (100 mL) and the solution was brought to pH 7 with 2M NaOH (20 mL). A GdCl3 solution (0.0087 mol) was slowly added at RT, adjusting the pH at 7 with 2M NaOH and checking the complexation with xylenol orange. Once the complexation was completed, the solution was concentrated and purified on resin Amberlite XAD 1600 eluting with water-acetonitrile gradient, in order to remove salts and impurities. After freeze-drying the pure compound was obtained as white solid (6.79 g, yield 94%). The product was characterized in HPLC; the obtained HPLC chromatogram, characterized by several peaks, is shown in FIG. 1

A compound totally equivalent to compound VI, consisting of an isomeric mixture with a HPLC chromatogram substantially superimposable to that of FIG. 1 is obtained even by using (S)-methyl α-bromoglutarate obtained starting from L-glutamic acid.

Example 2: Synthesis of Gadopiclenol (Isomeric Mixture)

Gadopiclenol as an indiscriminate mixture of stereoisomers has been prepared as disclosed in EP11931673 B1 by coupling the isomeric mixture of Gd(PCTA-tris-glutaric acid) obtained from Example 1 with racemic isoserinol according to the following synthetic Scheme 2:

Scheme 2

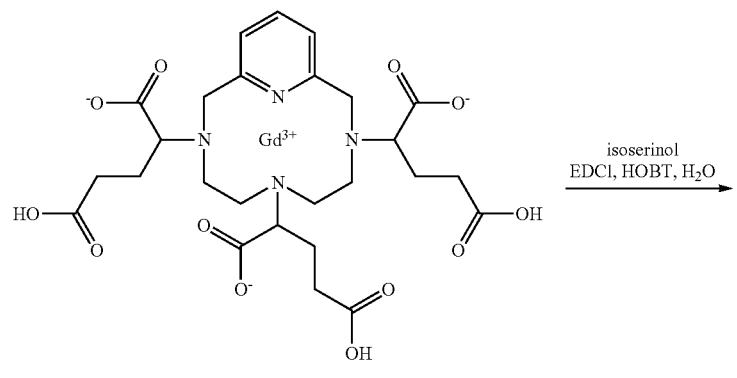

VI

-continued

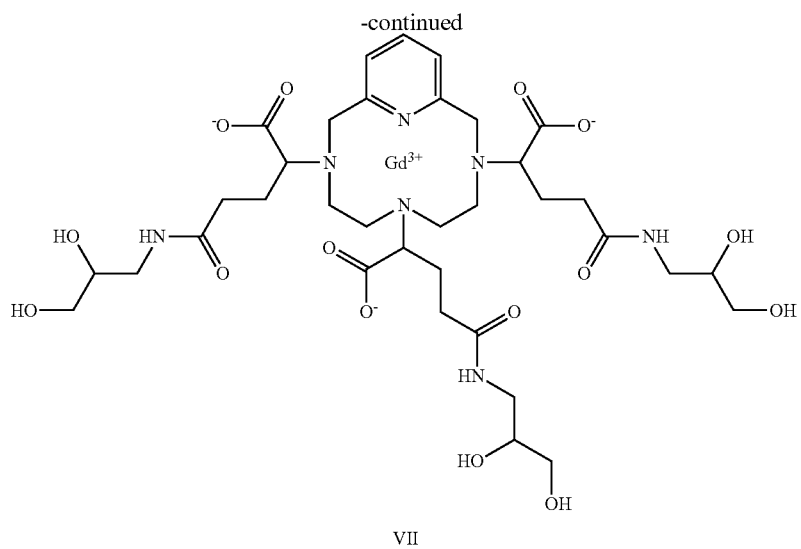

VII

Preparation of Compound VII

Compound VI (0.90 g, 0.0011 mol) obtained from Example 1 was added to a solution of racemic isoserinol (0.40 g, 0.0044 mol) in water adjusted to pH 6 with conc. HCl. Then N-ethyl-N'-(3-dimethylaminopropyl)carbodiimide hydrochloride (EDCI·HCl) (1.0 g, 0.0055 mol) and hydroxybenzotriazole (HOBT) (0.12 g, 0.00088 mol) were added and the resulting solution was stirred at pH 6 and RT for 24 h. The product was then purified on preparative HPLC on silica $C_{18}$, eluting with water/acetonitrile gradient. Fractions containing the pure compound were concentrated and freeze-dried, obtaining a white solid (0.83 g, yield 78%). The product was characterized in HPLC; the obtained HPLC chromatogram is shown in FIG. 4a.

Example 3: Isolation of the Enantiomers Pair Related to the Peak C

Compound VI obtained as described in Example 1 (step d) (1.0 g, 0.0013 mol) was dissolved in water (4 mL) and the solution was acidified to pH 2-3 with conc. HCl. The obtained solution was loaded into a pre-packed column of silica C18 (Biotage® SNAP ULTRA C18 120 g, HP-sphere C18 25 µm) and purified with an automated flash chromatography system eluting with deionized water (4 CV) and then a very slow gradient of acetonitrile. Fractions enriched of the enantiomers pair related to the peak C were combined, concentrated and freeze-dried obtaining a white solid (200 mg).

The HPLC chromatogram of the obtained enriched enantiomers pair C is shown in FIG. 2.

Figure 3:
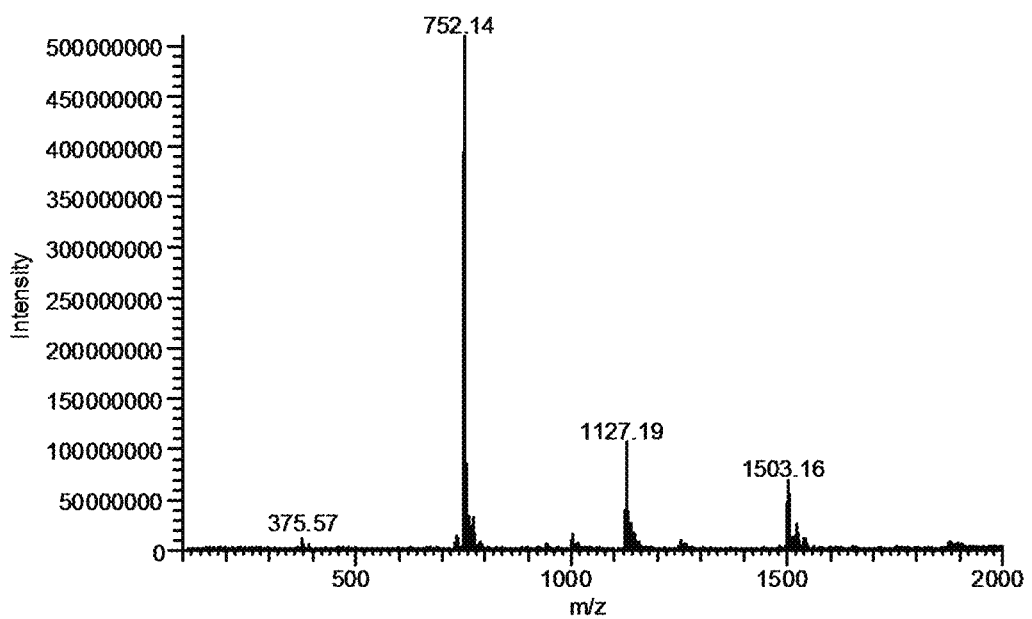
FIG. 3 shows the MS spectrum of the major peak of FIG. 2. m/z ratio Gd(H$_4$L)+:752.14 m/z.

Corresponding MS spectrum (Gd(H$_4$L)+:752.14 m/z) is provided in FIG. 3

Example 4: Coupling of the Enantiomers Pair C with Isoserinol a) Coupling of the Enantiomers Pair C with R-Isoserinol.

Enriched enantiomers pair C collected e.g. as in Example 3 (34 mg, titer 90%, 0.040 mmol) was dissolved in deionized water (5 mL), and R-isoserinol (16 mg, 0.17 mmol) was added adjusting the pH at 6 with HCl 1M. Then, EDCI·HCl (39 mg, 0.20 mmol) and HOBT (3 mg, 0.02 mmol) were added and the solution was stirred at RT at pH 6 for 48 h. The solution was concentrated and loaded to pre-packed silica C18 column (Biotage® SNAP ULTRA C18 12 g, HP-sphere C18 25 µm), eluting with water/acetonitrile gradient using an automated flash chromatography system. Fractions containing the pure product, or showing a major peak at the HPLC with area greater than 90%, were combined, concentrated and freeze-dried giving a white solid (21 mg, yield 54%).

The HPLC chromatogram of the obtained product is shown in FIG. 6b.

b) Coupling of the Enantiomers Pair C with S-Isoserinol

Enriched enantiomers pair C collected e.g. as in Example 3 (55 mg, titer 90%, 0.066 mmol) was dissolved in deionized water (5 mL), and S-isoserinol (34 mg, 0.29 mmol) was added adjusting the pH at 6 with 1M HCl. Then, EDCI·HCl (64 mg, 0.33 mmol) and HOBT (4.5 mg, 0.033 mmol) were added and the solution was stirred at RT at pH 6 for 48 h. The solution was concentrated and loaded to pre-packed silica C18 column (Biotage® SNAP ULTRA C18 12 g, HP-sphere C18 25 µm), eluting with water/acetonitrile gradient using an automated flash chromatography system. Fractions containing the pure product, or showing a major peak at the HPLC with area greater than 90%, were combined, concentrated and freeze-dried giving a white solid (52 mg, yield 81%).

HPLC chromatogram of the obtained product is shown in FIG. 6c.

c) Coupling of the Enantiomers Pair C with Racemic Isoserinol.

The enriched enantiomers pair C collected e.g. as in Example 3 (54 mg, titer 90%, 0.065 mmol) was dissolved in deionized water (5 mL), and racemic isoserinol (27 mg, 0.29 mmol) was added adjusting the pH at 6 with 1M HCl. Then, EDCI·HCl (62 mg, 0.32 mmol) and HOBT (4.3 mg, 0.032 mmol) were added and the solution was stirred at RT at pH 6 for 24 h. The solution was concentrated and loaded to pre-packed silica C18 column (Biotage® SNAP ULTRA C18 12 g, HP-sphere C18 25 µm), eluting with water/acetonitrile gradient using an automated flash chromatography system. Fractions containing the pure product, or showing a major peak at the HPLC with area greater than 90%, were combined, concentrated and freeze-dried giving a white solid (60 mg, yield 95%).

HPLC chromatogram of the obtained product is shown in FIG. 6d.

Example 5: Stereoselective Synthesis of the RRR Gd(PCTA-Tris-Glutaric Acid) (Compound XII)

RRR enriched Gd(PCTA-tris-glutaric acid) acid has been prepared by following the synthetic Scheme 3 below

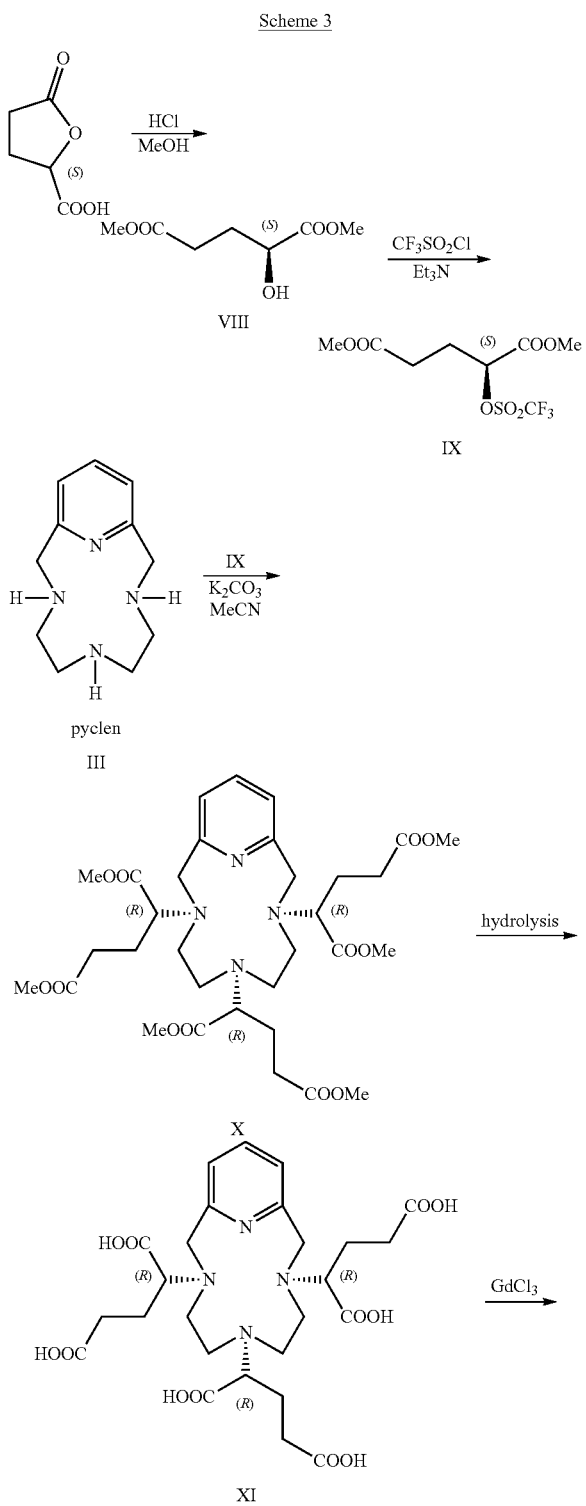

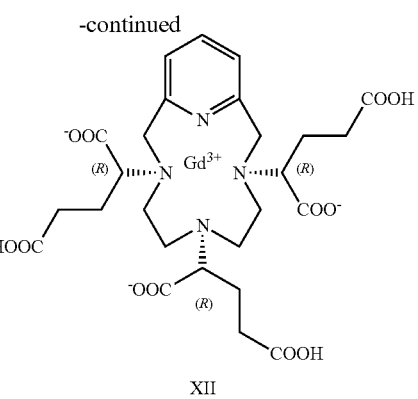

XII comprising:

a) Preparation of Compound VIII

The preparation was carried out as reported in Tetrahedron 2009, 65, 4671-4680.

In particular: 37% aq. HCl (50 µL) was added to a solution of (S)-(+)-5-oxotetrahydrofuran-2-carboxylic acid (2.48 g, 0.019 mol) (commercially available) in anhydrous methanol (20 mL). The solution was refluxed under N2 atmosphere for 24 h. After cooling in ice, NaHCO$_3$ was added, the suspension was filtered, concentrated and purified on silica gel with hexanes/ethyl acetate 1:1. Fractions containing the pure product were combined and concentrated, giving a colorless oil (2.97 g, yield 89%).

b) Preparation of Compounds IX and X

Compound VIII (445 mg, 2.52 mmol) obtained at step a) was dissolved in anhydrous dichloromethane (6 mL) and triethylamine (0.87 mL, 6.31 mmol) was added. The solution was cooled at −40° C. and then (triflic) trifluoromethansulfonic anhydride (0.49 mL, 2.91 mmol) was slowly added. The dark solution was stirred at −40° C. for 1 h, then a solution of Compound III (104 mg, 0.506 mmol) in anhydrous dichloromethane (3 mL) and triethylamine (1 mL, 7.56 mmol) were added and the solution was slowly brought to RT and stirred at RT overnight. The organic solution was then washed with 2M HCl (4×10 mL), the aqueous phase was extracted again with dichloromethane (3×10 mL). The organic phases were combined and concentrated in vacuum, obtaining 400 mg of a brown oil that was used in the following step with no further purification.

c) Preparation of Compound XI

Compound X (400 mg, 0.59 mmol) was dissolved in methanol (2.5 mL) and 5M NaOH (2.5 mL). The brown solution was heated at 80° C. for 22 h to ensure complete hydrolysis. Methanol was concentrated, the solution was brought to pH 1 with concentrated HCl and purified through an automated flash chromatography system with a silica C18 pre-packed column (Biotage® SNAP ULTRA C18 12 g, HP-sphere C18 25 µm), eluting with deionized water/acetonitrile gradient. Fractions containing the pure product were combined, concentrated and freeze-dried (64 mg, yield 18%). The HPLC showed a major peak.

d) Compound XII

Compound XI (32 mg, 0.054 mmol) was dissolved in deionized water (4 mL) and the pH was adjusted to 7 with 1M NaOH. GdCl3.6H$_2$O (20 mg, 0.054 mmol) was added and the pH was adjusted to 7 with 0.1 M NaOH. The clear solution was stirred at RT overnight and the end of the complexation was checked by xylenol orange and HPLC. The HPLC of the crude showed the desired RRR isomer as major peak: about 80% in area %. The mixture was brought to pH 2 with concentrated HCl and purified through an automated flash chromatography system with a silica C18 pre-packed column (Biotage® SNAP ULTRA C18 12 g, HP-sphere C18 25 μm), eluting with deionized water/acetonitrile gradient. Fractions containing the pure product were combined, concentrated and freeze-dried (36 mg, yield 90%).

By reaction of the collected compound with isoserinol e.g. by using the procedure of the Example 2, the corresponding RRR amide derivative can then be obtained.

Example 6: Stereoselective Synthesis of the SSS Gd(PCTA-Tris-Glutaric Acid) (Compound XVII)

SSS enriched Gd(PCTA-tris-glutaric acid) acid has been similarly prepared by following the synthetic Scheme 4 below

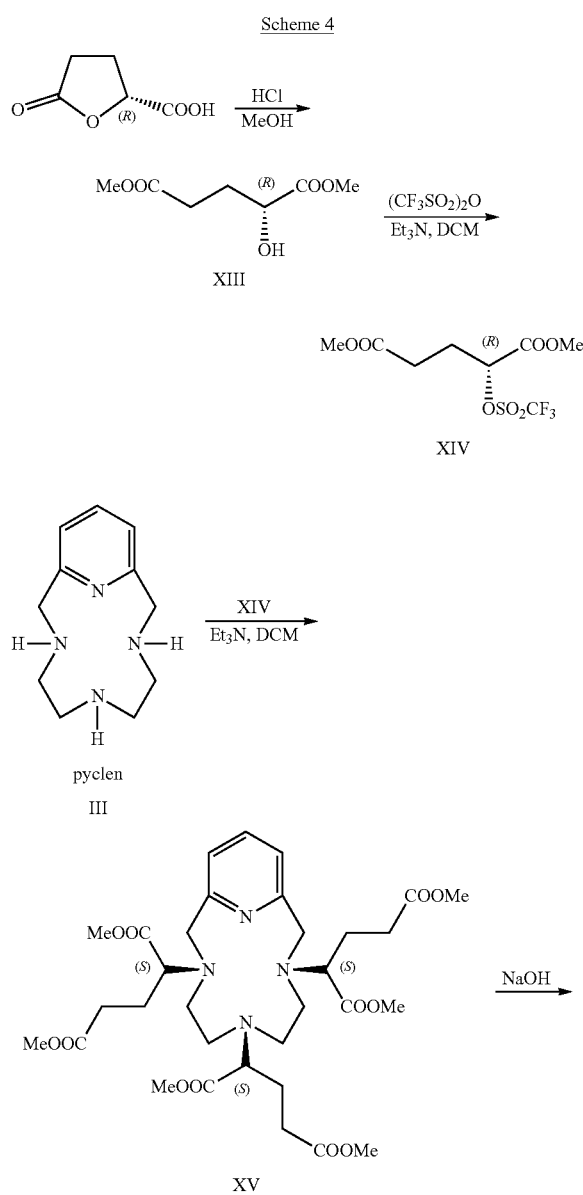

comprising:

a) Preparation of Compound XIII

37% aq. HCl (100 μL) was added to a solution of (R)-(−)-5-oxotetrahydrofuran-2-carboxylic acid (5.0 g, 0.038 mol) (commercially available) in anhydrous methanol (45 mL). The solution was refluxed under N2 atmosphere for 24 h. After cooling in ice, NaHCO₃ was added, the suspension was filtered, concentrated and purified on silica gel with hexanes/ethyl acetate 1:1. Fractions containing the pure product were combined and concentrated, giving a colorless oil (6.7 g, yield 99%).

b) Preparation of Compounds XIV and XV

Compound XIII (470 mg, 2.67 mmol) was dissolved in anhydrous dichloromethane (6 mL) and trimethylamine (0.93 mL, 6.67 mmol) was added. The solution was cooled down at −40° C. and then trifluoromethanesulfonic anhydride (0.50 mL, 3.07 mmol) was slowly dropped. The dark solution was stirred at −40° C. for 1 h, then Compound III (140 mg, 0.679 mmol) and trimethylamine (0.93 mL, 6.67 mmol) were added and the solution was slowly brought to RT overnight. The organic solution was then washed with water (3×5 mL) and 2M HCl (4×5 mL). The aqueous phase was extracted again with dichloromethane (3×10 mL). the organic phases were combined and concentrated in vacuum, obtaining 350 mg of a brown oil that was used in the following step with no further purification.

c) Preparation of Compound XVI

Compound XV (350 mg, 0.514 mmol) was dissolved in methanol (4.5 mL) and 5M NaOH (4.5 mL). The obtained brown solution was heated at 80° C. for 16 h to ensure complete hydrolysis. Methanol was concentrated, the solution was brought to pH 2 with concentrated HCl and purified through an automated flash chromatography system with a silica C18 pre-packed column (Biotage® SNAP ULTRA C18 12 g, HP-SPHERE C18 25 μm), eluting with a water/acetonitrile gradient. Fractions containing the pure product were combined, concentrated and freeze-dried (52 mg, yield 17%). The HPLC showed a major peak.

d) Preparation of Compound XVII

Compound XVI (34 mg, 0.057 mmol) was dissolved in deionized water (5 mL) and the pH was adjusted to 7 with 1 M HCl. GdCl3.6H$_2$O (20 mg, 0.0538 mmol) was added and the pH was adjusted to 7 with 0.1 M NaOH. The solution was stirred at RT overnight and the end of complexation was checked by xylenol orange and HPLC. The HPLC of the crude showed the desired SSS isomer as major peak: about 85% in area %. The solution was brought to pH 2.5 with concentrated HCl and purified through an automated flash chromatography system with a silica C18 pre-packed column (Biotage® SNAP ULTRA C18 12 g, HP-SPHERE C18 25 μm), eluting with a water/acetonitrile gradient. Fractions containing the pure product SSS were combined, concentrated and freeze-dried (39 mg, yield 87%).

Example 7: Kinetic Studies of the Dissociation Reactions of Gd(PCTA-Tris-Glutaric Acid) (Isomeric Mixture) in 1.0 M HCl Solution (25° C.)

The kinetic inertness of a Gd(III)-complex is characterized either by the rate of dissociation measured in 0.1-1.0 M HCl or by the rate of the transmetallation reaction, occurring in solutions with Zn(II) and Cu(II) or Eu(III) ions. However, the dissociation of lanthanide(III)-complexes formed with macrocyclic ligands is very slow and generally proceeds through a proton-assisted pathway without the involvement of endogenous metal ions like Zn$^{2+}$ and Cu$^{2+}$.

We characterized the kinetic inertness of the complex Gd(PCTA-tris-glutaric acid) by the rates of the dissociation reactions taking place in 1.0 M HCl solution. The complex (isomeric mixture from Example 1) (0.3 mg) was dissolved in 2.0 mL of 1.0 M HCl solution and the evolution of the solution kept at 25° C. was followed over time by HPLC. The HPLC measurements were performed with an Agilent 1260 Infinity II system by use of the analytical Procedure 1.

The presence of a large excess of H$^+$ ([HCl]=1.0 M), guarantees the pseudo-first order kinetic conditions.

$$GdL + yH^+ \rightleftharpoons Gd^{3+} + H_yL \quad y=7 \text{ and } 8 \quad \text{(Eq. 1)}$$

where L is the protonated PCTA-tri-glutaric acid, free ligand, and y is the number of protons attached to the ligand.

The HPLC chromatogram of Gd(PCTA-tris-glutaric acid) is characterized by the presence of four signals (A, B, C and D) having the same m/z ratio (Gd(H$_4$L)+:752.14 m/z) in the MS spectrum. Each of these peaks is reasonably ascribable to one of the 4 pairs of enantiomers generated by the three stereocenters on the three glutaric arms of the molecule, formerly identified in Table 1. The HPLC chromatogram of this complex in the presence of 1.0 M HCl changes over time: in particular, the areas of peaks A, B, C, and D decrease, although not in the same way for the different peaks, while new signals corresponding to non-complexed diastereoisomers are formed and grow over time. Differences in the decrease of the integral areas of the peaks can be interpreted by a different dissociation rate of the enantiomer pairs associated to the different peaks.

In the presence of [H+] excess the dissociation reaction of enantiomer pairs of Gd(PCTA-tris-glutaric acid) can be treated as a pseudo-first-order process, and the rate of the reactions can be expressed with the following Eq. 2, where $k_A$, $k_B$, $k_C$ and $k_D$ are the pseudo-first-order rate constants that are calculated by fitting the area-time data pair, and [A]$_t$, [B]$_t$, [C]$_t$ and [D]$_t$ are the total concentration of A, B, C and D compounds at time t.

$$-\frac{d[A]}{dt} = k_A[A]_t; \; -\frac{d[B]}{dt} = k_B[B]_t; \quad \text{(Eq. 2)}$$

$$-\frac{d[C]}{dt} = k_C[C]_t; \; -\frac{d[D]}{dt} = k_D[D]_t$$

Figure 7:
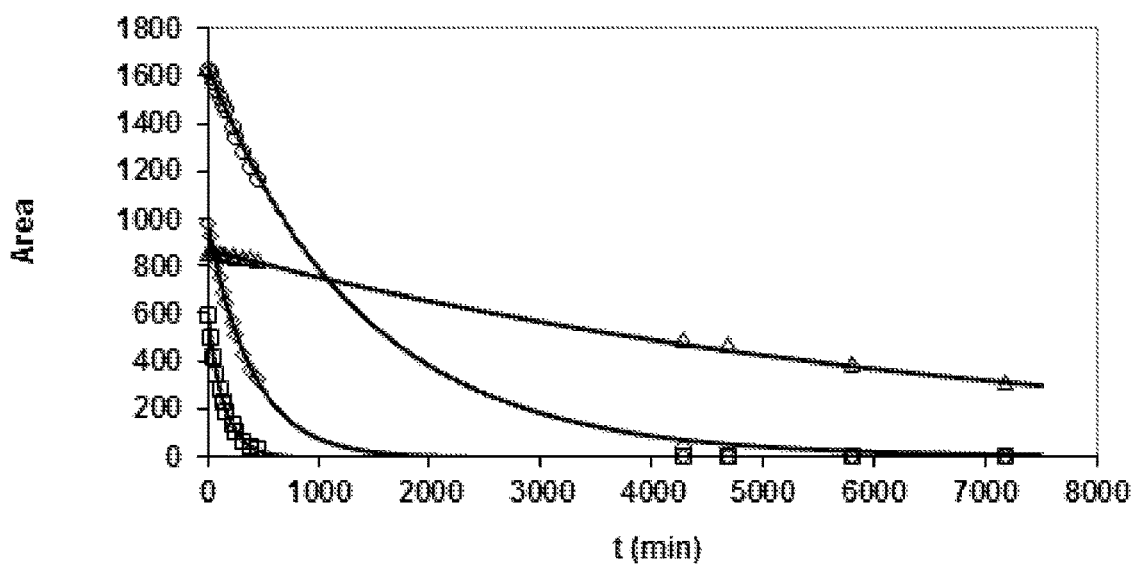
FIG. 7 refers to the test of Example 7 and shows the HPLC area values of the peaks A (◇), B (□), C (△) and D (○) as a function of time ([GdL]=0.2 mM, [HCl]=1.0 M, 25° C.).
Figure 8:
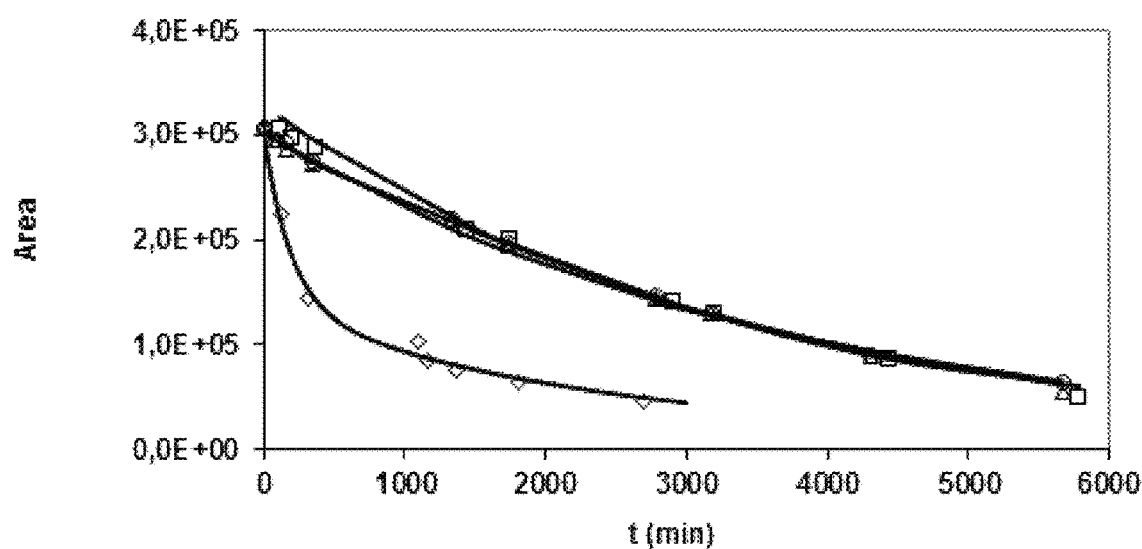
FIG. 8 refers to the test of Example 8 and shows the HPLC area values as a function of time: total area of the isomeric mixture (◇); RRR/SSS Gd(PCTA-tris-glutaric acid)+R isoserinol (□); RRR/SSS Gd(PCTA-tris-glutaric acid)+S isoserinol (△); RRR/SSS Gd(PCTA-tris-glutaric acid)+racemic isoserinol (○). ([GdL]=0.2 mM, [HCl]=1.0 M, 25° C.).

The decrease of the area values of signals of A, B, C, and D has been assessed and plotted over time. Area values of A, B, C and D signals as a function of time are shown in FIG. 7.

Area value at time t can be expressed by the following equation:

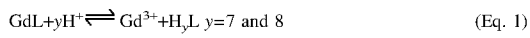

$$A_t = A_e + (A_0 - A_e)e^{-kxt} \quad \text{(Eq. 3)}$$

where $A_t$, $A_0$ and $A_e$ are the area values at time t, at the beginning and at the end of the reactions, respectively. $k_X$ pseudo-first-order rate constants ($k_X = k_A$, $k_B$, $k_C$ and $k_D$) characterizing the dissociation rate of the different enantiomer pairs of Gd(PCTA-tris-glutaric acid) complex were calculated by fitting the area—time data pairs of FIG. 7 to the above equation 3. $k_X$ rate constants and half-lives ($t_{1/2} = \ln 2/k_X$) are thus obtained, as well as the average the half-life value for the isomeric mixture of Gd(PCTA-tris-glutaric acid), calculated by considering the percentage composition of the mixture. Obtained values are summarized in the following Table 2, and compared with corresponding values referred in the literature for some reference contrast agents. (Gd-DOTA or DOTAREM™)

TABLE 2

Rate constants ($k_x$) and half-lives ($t_{1/2} = \ln 2/k_x$) characterizing the acid catalyzed dissociation of the different stereoisomers of Gd(PCTA-tris-glutaric acid), Dotarem ® and Eu(PCTA) in 1.0M HCl (pH 0) ( 25° C.)

| | A | B | C | D |
|---|---|---|---|---|
| $k_x$ (s$^{-1}$) | (4.5 ± 0.1) × 10$^{-5}$ | (1.1 ± 0.1) × 10$^{-4}$ | (1.6 ± 0.1) × 10$^{-6}$ | (1.2 ± 0.1) × 10$^{-5}$ |
| $t_{1/2}$ (hour) | 4.28 ± 0.03 | 1.76 ± 0.02 | 120 ± 3 | 15.8 ± 0.5 |
| $t_{1/2}$ (hour) average Dotarem [a] | | 10.5 | | |
| $k_1$ (s$^{-1}$) | | 8.0 × 10$^{-6}$ | | |
| $t_{1/2}$ (hour) Eu(PCTA) [b] | | 23 hour | | |
| $k_1$ (s$^{-1}$) | | 5.08 × 10$^{-4}$ | | |
| $t_{1/2}$ (hour) | | 0.38 hour | | |

[a] Inorg. Chem. 1992, 31,1095-1099.
[b] Tircso, G. et al. Inorg Chem 2006, 45 (23), 9269-80.

The results of Table 2 clearly show that $k_X$ rate constant characterizing the acid catalyzed dissociation of the pair of enantiomers associated to the peak C is significantly smaller than that of stereo isomers of the Gd(PCTA-tris-glutaric acid) complex associated to the peaks A, B and D. Comparison of the half-life values ($t_{1/2}$) presented in Table 2 indicates that the $t_{1/2}$ value of the enantiomers pair associated to the peak C (of the Gd(PCTA-tris-glutaric acid)) is about 28, 68 and 8 times higher than the $t_{1/2}$ values of those associated to the peaks A, B and D, respectively. Moreover, the $t_{1/2}$ value of the enantiomers pair C of Gd(PCTA-tris-glutaric acid) is somewhat higher than the $t_{1/2}$ value of Gd(DOTA) ($t_{1/2}$=23 h in 1.0 M HCl).

Example 8: Kinetic Studies of the Dissociation Reactions of Gadopiclenol (Isomeric Mixture from Example 2), and of the Complex Compounds Obtained by Coupling of Enantiomers Pair C Respectively with R, S, and Racemic Isoserinol in 1.0 M HCl Solution (25° C.)

The kinetic inertness of all complexes was characterized by the rates of the dissociation reactions taking place in 1.0 M HCl solution. For each batch the complex (0.4 mg) was dissolved in 2.0 mL of 1.0 M HCl solution and the dissociation reactions at 25° C. was followed over time by HPLC. The HPLC measurements were performed with Thermo Finnigan LCQ DECA XPPlus system according to the analytical Procedure 2.

HPLC chromatogram of Gadopiclenol collected as isomeric mixture from Example 2 is characterized by the presence of 4 major peaks (identified for convenience as A', B', C' and D') having the same MS and UV-Vis spectra. However, there is only one signal in the HPLC chromatogram of the complex compounds obtained by coupling the enantiomers pair C with isoserinol, whether it is R, S isoserinol or racemic-isoserinol (FIG. 6). Since, as observed, the chirality of the isoserinol pendant has no influence on the retention time of coupled diastereoisomers, the presence of 4 signals in the HPLC chromatograms of Gadopiclenol (isomeric mixture) could be interpreted by the presence of 4 enantiomer pairs formed with the stereocenters of the of the glutaric acid residue: 1) RRR-SSS (Signal D'), 2) RSR-SRS, 3) RRS-SSR and 4) RSS-SRR.

To obtain information about the kinetic inertness of all above complexes, their dissociation reactions were investigated in the presence of a large excess of H+([HCl]=1.0 M) in order to ensure the occurrence of pseudo-first order conditions. The progress of the reactions was checked by HPLC over time, plotting the area values of the peaks of the complex as a function of time, as above discussed in Example 7 for Gd(PCTA-tris-glutaric acid) isomers.

As expected, the integral values of A', B', C', and D' decrease over time, whereas the peak of the free ligand increases. Since area values in the HPLC chromatograms are directly proportional to the concentration of Gadopiclenol (isomeric mixture), the half-life of the dissociation reaction of Gadopiclenol (isomeric mixture) can be estimated from the half of the sum of the area values. The half-life of Gadopiclenol (isomeric mixture) was found to be 5.2 hours at 25° C. and pH 0 (1.0 M HCl). The half-life of complexes obtained by coupling the enantiomers pair C with R, S and racemic-isoserinol was also calculated from the half of the area values in the HPLC chromatograms. The half-life of complexes obtained by coupling the enantiomers pair C with R, S and racemic-isoserinol was found to be 41, 43 and 44 hours at 25° C. and pH 0 (1.0 M HCl). The pseudo-first order rate constant ($k_x$) characterizing the rate of the dissociation reaction of complexes obtained by coupling the enantiomers pair C with R, S and racemic-isoserinol can also be calculated by the fitting of the area-time kinetic data with the equation 3, as above said $$A_t = A_e + (A_0 - A_e) e^{-k_X t} \quad (Eq.\ 3)$$

where $A_t$, $A_0$ and $A_e$ are the area values at time t, at the beginning and at the end of the reactions, whereas $k_X$ pseudo-first order rate constant (half-life: $t_{1/2}$, $t_{1/2} = \ln2/k_X$) characterizing the acid catalysed dissociation reactions of complexes obtained by coupling the enantiomers pair C with R, S and racemic-isoserinol. $k_x$ and $t_{1/2}$ values obtained by the fitting of the kinetic data are summarized in the following Table 3, and compared with corresponding values quoted in the literature for some reference contrast agents.

The comparison of $t_{1/2}$ values of complexes obtained by coupling enantiomers pair C with R, S and racemic-isoserinol, estimated from the area values and calculated by the fitting of the area-time kinetic data are in a very good agreement. $t_{1/2}$ values presented in Table 3 clearly indicate that the dissociation half-life of the D' isomers obtained by coupling the enantiomers pair C isomer with R, S, and racemic isoserinol are about identical and 8 times higher than that measured for Gadopiclenol (isomeric mixture), which confirms that the higher kinetic inertness of the RRR-SSS Gd(PCTA-tris-glutaric acid) is substantially maintained even after its coupling with isoserinol. Moreover, the $t_{1/2}$ values of complexes obtained by coupling the enantiomers pair C with R, S, and racemic-isoserinol also indicate that the chirality of the isoserinol pendant has no influence on the kinetic inertness of the final complex.

TABLE 3

Rate constants ($k_x$) and half-lives ($t_{1/2} = \ln2/k_x$) characterizing the acid catalyzed dissociation of Gadopiclenol (isomeric mixture), complex compounds obtained by coupling enantiomers pair C with R, S and racemic-isoserinol, Dotarem and Eu(PCTA) in 1.0M HCl (25° C.)

| Gadopiclenol (isomeric mixture) | |
|---|---|
| $t_{1/2}$ (hour)* | 5.2 |
| Enantiomers pair C + R-isoserinol | |
| $t_{1/2}$ (hour)* | 41 |
| $k_x \cdot (s^{-1})$ | $(4.9 \pm 0.4) \times 10^{-6}$ |
| | ($t_{1/2}$ = 39 hours)** |
| Enantiomers pair C + S-isoserinol | |
| $t_{1/2}$ (hour)* | 43 |
| $k_x (s^{-1})$ | $(4.6 \pm 0.3) \times 10^{-6}$ |
| | ($t_{1/2}$ = 42 hours)** |
| Enantiomers pair C + racemic-isoserinol | |
| $t_{1/2}$ (hour)* | 44 |
| $k_x (s^{-1})$ | $(4.5 \pm 0.4) \times 10^{-6}$ |
| | ($t_{1/2}$ = 43 hours)** |
| Dotarem | |
| $t_{1/2}$ (hour) | 23 hour |
| $k_x (s^{-1})$ | $8.0 \times 10^{-6}$ |
| Eu(PCTA) | |
| $t_{1/2}$ (hour) | 0.38 hour |
| $k_x \cdot (s^{-1})$ | $5.08 \times 10^{-4}$ |

*calculated from the half of the total area
**calculated from the fitting of the equation Example 9: Relaxometric Properties The relaxometric properties of the PCTA-based complex compounds according to the invention have been measured at different magnetic field strengths, i.e. 0.47 and 1.41 T, at 37° C. and in different media (water and human plasma) and compared with relaxivity values measured, at the same conditions, for Gd-Complex having an analogous coordination cage.

Materials
Apparatus

The longitudinal water proton relaxation rate ($R_1 = 1/T_1$) was measured at 0.47 T with a Minispec MQ-20 spectrometer (Bruker Biospin, Germany) operating at a proton Larmor frequency of 20 MHz; MR experiments at 1.41 T were performed using a Minispec MQ-60 spectrometer (Bruker Biospin, Germany) operating at a proton Larmor frequency of 60 MHz.

Methods

Sample Preparation

All test articles were used as supplied and diluted in the selected medium (water or human plasma) by weighting the required amount of paramagnetic chelated complex to get a 5 or 10 mM starting solution.

Relaxivity Measurements

Five different concentration samples (0.1, 0.25, 0.5, 0.75 and 1 mM) for each medium have been prepared by further dilution of the starting 5 or 10 mM solution.

Relaxation Measurement

Relaxivity measurements were performed at 0.47 T and 1.41 T at a preset temperature sample of 37° C., kept constant by means of a thermostatic bath connected to the sample holder of the spectrometer. The five sample solutions have been preliminary pre-heated at 37° C. in an external thermostatic bath and then left 10 minutes inside the internal bath to assure the stabilization of the temperature. Longitudinal relaxation time $T_1$ was measured by means of a standard inversion recovery sequence, where the inversion time (TI) was varied from 10 ms to at least 5 times $T_1$ in 15 steps. Statistical analysis (mono-exponential fitting for $T_1$ measurement, linear fitting for the evaluation of longitudinal relaxivity) was performed by Mathematica® (Wolfram, USA). Errors on the estimated parameters were evaluated by the fitting procedure.

Results

The following Table 4 shows the relaxivity value $r_1$ value reported in EP 1931673 B1 for the Gd(PCTA-tris-glutaric acid) (isomeric mixture) and the corresponding $r_1$ value obtained, under same conditions, for purified fractions of RRR/SSS Gd(PCTA-tris-glutaric acid)

TABLE 4

| Compound | $r_1$ (mM$^{-1}$s$^{-1}$) H$_2$O, 0.5T, 37° C. |
|---|---|
| Gd(PCTA-tris-glutaric acid) isomeric mixture | 7.2* |
| RRR/SSS Gd(PCTA-tris-glutaric acid) | 9.3 ± 0.1 |

*value reported in EP 1931673 B1

The following Table 5 summarizes the relaxivity values $r_1$ measured, both in H$_2$O and in HSA, at 37° C., for amide derivatives obtained by conjugation of RRR/SSS Gd(PCTA-tris-glutaric acid) with isoserinol, together with the stereochemistry of the serinol used for conjugation, compared with corresponding values quoted by the cited prior art for Gadopiclenol (isomeric mixture).

TABLE 5

| Compound | $r_1$ (mM$^{-1}$s$^{-1}$) H$_2$O, 0.5T, 37° C. | $r_1$ (mM$^{-1}$s$^{-1}$) HSA, 1.5T, 37° C. |
|---|---|---|
| Gadopiclenol (isomeric mixture) | 11* | 12.8 ± 1.3** |
| enantiomers pair C + racemic isoserinol | 13.0 ± 0.1 | 14.0 ± 0.2 |
| enantiomers pair C + R isoserinol | 12.9 ± 0.1 | 14.0 ± 0.3 |
| enantiomers pair C + S isoserinol | 12.9 ± 0.2 | 13.9 ± 0.2 |

*value reported in EP 1931673; a value of 11-12 mM$^{-1}$s$^{-1}$ is otherwise quoted for the same compound in EP 2988756;
*value reported in reported in Invest. Radiol. 2015, 50, 835-842

Obtained results from one side shows that the higher relaxivity measured for RRR/SSS Gd(PCTA-tris-glutaric acid) toward the corresponding isomeric mixture is substantially maintained for respective conjugated derivatives. On the other hand, these results are consistent with the fact that the stereochemistry of the isoserinol moiety does not affect the major properties of the final compound that are mainly associated with the stereochemistry of the glutaric arm.

Example 10: X-Ray Diffraction

Enantiomers Pair C

Crystal Preparation

Single crystals of formula {(C(NH$_2$)$_3$)$_2$[Gd(H$_3$L)(C$_2$O$_4$)]}0.5H$_2$O (where Gd(H$_3$L) is the tris-protonated RRR/SSS Gd(PCTA-tris-glutaric acid)) suitable for X-ray diffraction studies were grown from an aqueous solution of the RRR/SSS enriched compound C collected from Example 3 by slow evaporation of water. To promote crystallization, the two inner sphere water molecules of the Gd(PCTA-tris-glutaric acid) complex were replaced by oxalate anion and the related guanidinium salt was then crystallized from water. The starting solution was prepared by dissolving 49.6 mg (C(NH$_2$)$_3$)$_2$(C$_2$O$_4$) (2.5.0×10−4 mol) in an aqueous solution of the enriched compound C collected from Example 3 (1.0 mL; 0.0483 M GdH$_3$L aqueous solution 5.0×10$^{-5}$ mol). The pH was adjusted to 3.3 by the stepwise addition of solid H$_2$C$_2$O$_4$.

Crystals were isolated and XRD data were collected from at least five crystals, at the X-ray diffraction beamline (XRD1) of the Elettra Synchrotron, Trieste (Italy), with the procedure e.g. disclosed by Lausi A. et al., The European Physical Journal Plus, 2015, 130, 1-8. In particular: collected crystals were dipped in NHV oil (Jena Bioscience, Jena, Germany), frozen in liquid nitrogen and mounted on the goniometer head with kapton loops (MiTeGen, Ithaca, USA). When different crystal shapes were available, all of them were tested. Complete datasets were collected at 100 K (nitrogen stream supplied through an Oxford Cryostream 700—Oxford Cryosystems Ltd., Oxford, United Kingdom) through the rotating crystal method. Data were acquired using a monochromatic wavelength of 0.700 Å, on a Pilatus 2M hybrid-pixel area detector (DECTRIS Ltd., Baden-Daettwil, Switzerland).

Results

The structures were solved by the dual space algorithm implemented in SHELXT direct methods (Sheldrick G. M. (2015). "SHELXT—Integrated space-group and crystal-structure determination", Acta Crystallographica Section A, 71, 3-8). Fourier analysis and refinement were performed by the full-matrix least-squares methods based on F$^2$. Anisotropic thermal motion refinement has been used for all atoms. Hydrogen atoms were included at calculated positions with isotropic U$_{factors}$=1.2·U$_{eq}$ or U$_{factors}$=1.5·U$_{eq}$ for hydroxyl groups (U$_{eq}$ being the equivalent isotropic thermal factor of the bonded non hydrogen atom). Hydrogen atoms for solvent water molecules have not been included in the refined models since it was not possible to locate them unambiguously in electrondensity peaks of Fourier difference maps.

Essential crystal and refinement data are reported in the Table below.

TABLE 6

Crystallographic data and stereocenters configurations for {(C(NH$_2$)$_3$)$_2$[Gd(H$_3$L)(C$_2$O$_4$)]}•5H$_2$O datasets.

| | |
|---|---|
| Crystal system | Monoclinic |
| Space Group | P 2$_1$/c |

TABLE 6-continued

Unit cell a = 10.682(2) Å
b = 36.733(7) Å
c = 10.521(2) Å
α = 90°
β = 90.80(3)°
γ = 90°
Volume (Å3) 4127.9(14)
Final R indices [I > 2σ(I)] $R_1$ = 0.0281, $wR_2$ = 0.0700
$R_1 = \Sigma\ ||Fo]-|Fc||/\Sigma\ |Fo|, wR2 = \{\Sigma\ [w(Fo2-Fc2)2]/\Sigma\ [w(Fo2)2]\}^{1/2}$
Chiral centres configurations.

| Atom | Chiral center configuration |
|---|---|
| C7_2 | R |
| C14_2 | R |
| C21_2 | R |

Centrosymmetric space group P 2₁/c

Figure 9:
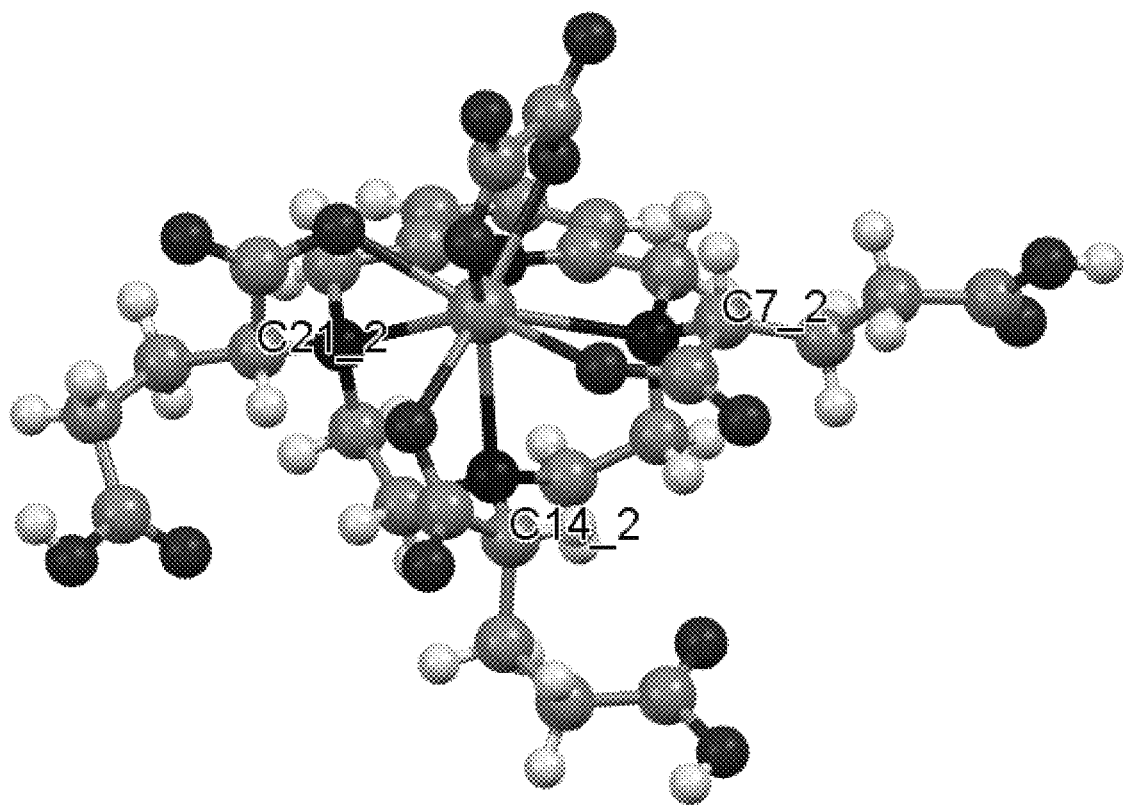
FIG. 9 shows to the X-ray structure of a single crystal of the Gd(PCTA-tris-glutaric acid)—oxalate ternary complex with guanidine counter ion of formula {(C(NH$_2$)$_3$)$_2$[Gd(PCTA-tris-glutaric acid)(C$_2$O$_4$)]}·1H$_2$O showing the chirality RRR of the (identified) chiral carbon atoms of the glutaric acid pendants.
Figure 10:
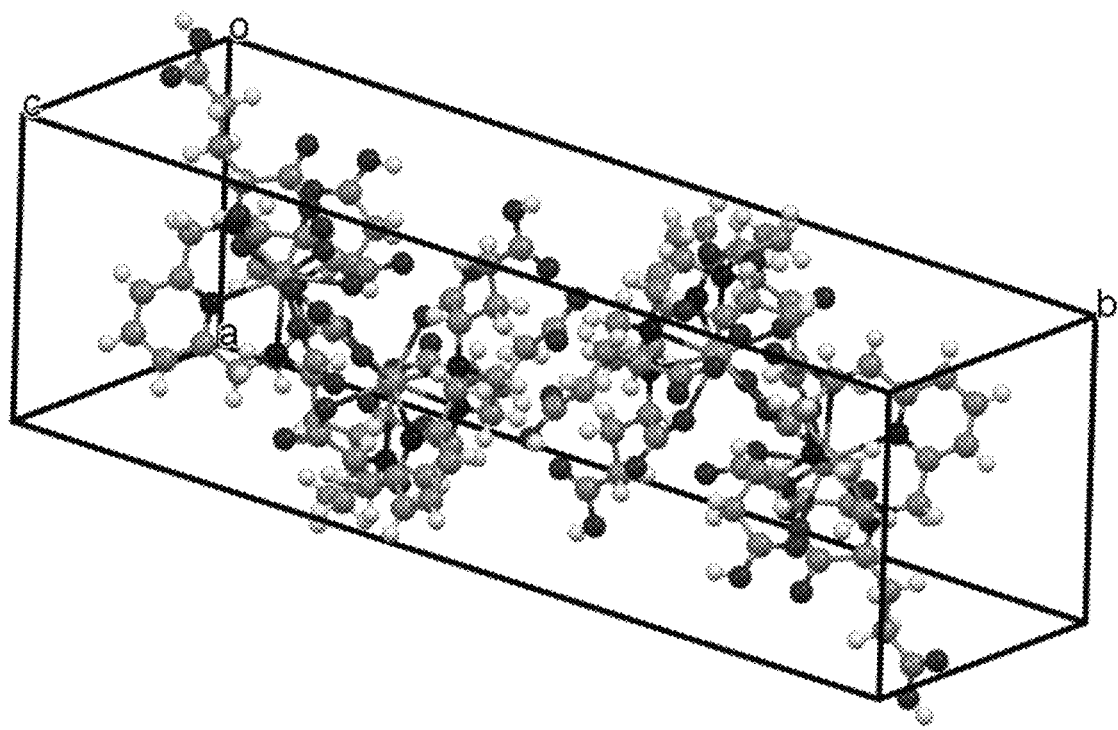
FIG. 10 shows the unit cell of the crystal of FIG. 9, containing 2RRR+2SSS complexes.

The X-ray structure of the {(C(NH₂)₃)₂[Gd(H₃L)(C₂O₄)]}·0.5H₂O complex and of the unit cell of the formed crystal are provided in FIGS. 9 and 10, respectively.

FIG. 10 shows that each unit cell contain 2RRR+2SSS complexes, wherein this means that each crystal contains isomers SSS and RRR in equimolar (50-50%) ratios.

Amide Derivative with Racemic Isoserinol

Single crystals of formula [GdC₃₅H₅₄N₇O₁₅][CH₆N₃]₂[CO₃]·18H₂O (GdL) (where GdL is RRR/SSS Gd(PCTA-tris-glutaric acid) conjugated with racemic isoserinol) suitable for X-ray diffraction studies were grown from an aqueous solution of the amide derivative of Gd(PCTA-tris-glutaric acid) with racemic isoserinol collected from Example 4 c). To promote crystallization, the two inner sphere water molecules of the final complex were replaced by carbonate anion and the related guanidinium salt was crystallized from water by slow diffusion of ethanol and diethyl ether at 4° C. In particular 1.0 molar equivalents (97 mg of the GdL complex and 9 mg of guanidine carbonate {C(NH₂)₃}₂CO₃) were dissolved in 1 mL H₂O, pH=10.5 with the slow diffusion of EtOH and Et₂O mixture.

Fifteen single crystals were isolated and XRD data collections of seven crystals were performed, at the X-ray diffraction beamline (XRD1) of the Elettra Synchrotron, Trieste (Italy), with the procedure e.g. disclosed by Lausi A. et al., The European Physical Journal Plus, 2015, 130, 1-8. In particular: collected crystals were dipped in NHV oil (Jena Bioscience, Jena, Germany), frozen in liquid nitrogen and mounted on the goniometer head with kapton loops (MiTeGen, Ithaca, USA). When different crystal shapes were available, all of them were tested. Complete datasets were collected at 100 K (nitrogen stream supplied through an Oxford Cryostream 700—Oxford Cryosystems Ltd., Oxford, United Kingdom) through the rotating crystal method. Data were acquired using a monochromatic wavelength of 0.700 Å, on a Pilatus 2M hybrid-pixel area detector (DECTRIS Ltd., Baden-Daettwil, Switzerland).

The structures were solved by direct methods. Fourier analysis and refinement were performed by the full-matrix least-squares methods based on $F^2$. Anisotropic thermal motion refinement has been used for all atoms. Hydrogen atoms were included at calculated positions with isotropic Ufactors=1.2·Ueq or Ufactors=1.5·Ueq for methyl and hydroxyl groups ($U_{eq}$ being the equivalent isotropic thermal factor of the bonded non-hydrogen atom). Hydrogen atoms for solvent water molecules have not been included in the refined models since it was not possible to locate them unambiguously in electrondensity peaks of Fourier difference maps.

TABLE 7

Crystallographic data and stereocenters configurations for GdL datasets.

Crystal system Trigonal
Space Group R −3
Unit cell a = 53.395(8) Å
b = 53.395(8) Å
c = 12.959(3) Å
α = 90°
β = 90°
γ = 120°
Volume (Å3) 31997(11)
Final R indices [I > 2σ(I) ]a R1 = 0.0554, wR2 = 0.1496
Stereocenters configurations in the ASU
C7 R C28A R-54(1)% occupancy C28B S-45(1)% occupancy)
C14 R C31A R-62(1)% occupancy C31B S-38(1)% occupancy
C21 R C34A R-50(1)% occupancy C34B S-50(1)% occupancy
a R1 = $\Sigma\ ||Fo|-|Fc||/\Sigma\ |Fo|, wR2 = \{\Sigma\ [w(Fo2-Fc2)2]/\Sigma\ [w(Fo2)2]\}^{1/2}$ With regard exploited procedures and elaborations see, for instance: Lausi A., Polentarutti M., Onesti S., Plaisier J. R., Busetto E., Bais G., Barba L., Cassetta A., Campi G., Lamba D., Pifferi A., Mande S. C., Sarma D. D., Sharma S. M., Paolucci G., The European Physical Journal Plus, 2015, 130, 1-8.

The X-ray structure of the D'-CO₃²⁻ complex and statistical analysis of the collected crystals are provided as FIG. 11.

The invention claimed is:

1. A process for the preparation of Gd(PCTA-tris-glutaric acid) enriched in the isomer [(αR,α'R,α"R)-α,α',α"-tris(2-carboxyethyl)-3,6,9,15-tetraazabicyclo[9.3.1]pentadeca-1(15),11,13-triene-3,6,9-triacetato(3-)-κN3,κN6,κN9,κN15,κO3,κO6,κO9]-gadolinium comprising:

a) preparing (2S)-2-[(trifluoromethylsulfonyl)oxy]pentanedioic acid dimethyl ester, of formula

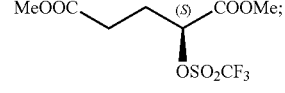

b) alkylating 3,6,9,15-tetraazabicyclo[9.3.1]pentadeca-1(15),11,13-triene of formula

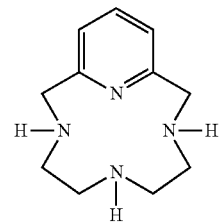 [SMILES: c1cc2nc(c1)CNCCNCCNC2]

with the (2S)-2-[(trifluoromethylsulfonyl)oxy]pentanedioic acid dimethyl ester collected from step a) to obtain a compound of formula X

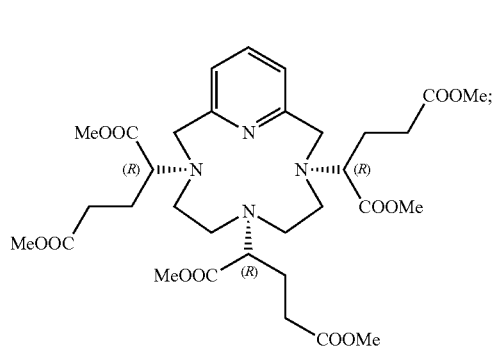

and
c) adding gadolinium or a salt thereof to convert the compound of formula X to the corresponding gadolinium complex.

2. A process for the preparation of Gd(PCTA-tris-glutaric acid) enriched in the isomer [(αS,α'S,α"S)-α,α',α"-tris(2-carboxyethyl)-3,6,9,15-tetraazabicyclo[9.3.1]pentadeca-1(15),11,13-triene-3,6,9-triacetato(3-)-κN3,κN6,κN9,κN15,κO3,κO6,κO9]-gadolinium comprising:

a') preparing (2R)-2-[(trifluoromethylsulfonyl)oxy]pentanedioic acid dimethyl ester, of formula

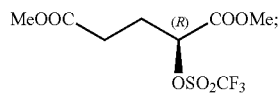

b') alkylating 3,6,9,15-tetraazabicyclo[9.3.1]pentadeca-1(15),11,13-triene of formula

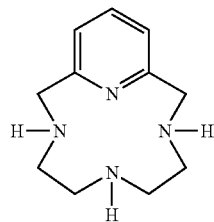

with the (2R)-2-[(trifluoromethylsulfonyl)oxy]pentanedioic acid dimethyl ester collected from step a') to obtain a compound of formula XV

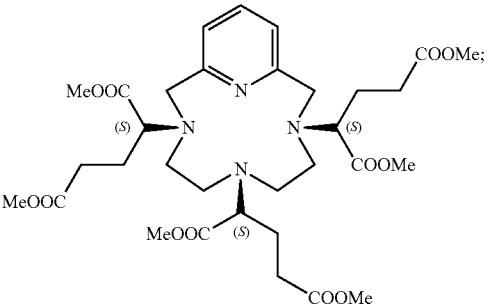

and
c') adding gadolinium or a salt thereof to convert the compound of formula XV to the corresponding gadolinium complex.

3. A process for the preparation of the amide derivative of Gd(PCTA-tris-glutaric acid) complex, said process comprising:

a') preparing a Gd(PCTA-tris-glutaric acid) complex according to claim 1; and b') conjugating the complex of step a') with an amine of formula $NHR_1R_2$, where $R_1$ is H or a $C_1$-$C_6$ alkyl, optionally substituted by 1-4 hydroxyl groups; and $R_2$ is a $C_1$-$C_6$ alkyl optionally substituted by 1-4 hydroxyl groups, to obtain the corresponding amide derivative.

4. A process for the preparation of the amide derivative of Gd(PCTA-tris-glutaric acid) complex, said process comprising:

a') preparing a Gd(PCTA-tris-glutaric acid) complex according to claim 2; and b') conjugating the complex of step a') with an amine of formula $NHR_1R_2$, where $R_1$ is H or a $C_1$-$C_6$ alkyl, optionally substituted by 1-4 hydroxyl groups; and $R_2$ is a $C_1$-$C_6$ alkyl optionally substituted by 1-4 hydroxyl groups, to obtain the corresponding amide derivative.

* * * * *

UNITED STATES PATENT AND TRADEMARK OFFICE
CERTIFICATE OF CORRECTION

PATENT NO. : 12,036,289 B2
APPLICATION NO. : 17/199122
DATED : July 16, 2024
INVENTOR(S) : Roberta Napolitano et al.

Page 1 of 1

It is certified that error appears in the above-identified patent and that said Letters Patent is hereby corrected as shown below:

In the Claims

Claim 1 at Column 43, Line 23 should read "complex by hydrolyzing the compound of formula X and adding a gadolinium salt." instead of "complex."

Claim 2 at Column 43, the structure at Lines 30-35 should read

" 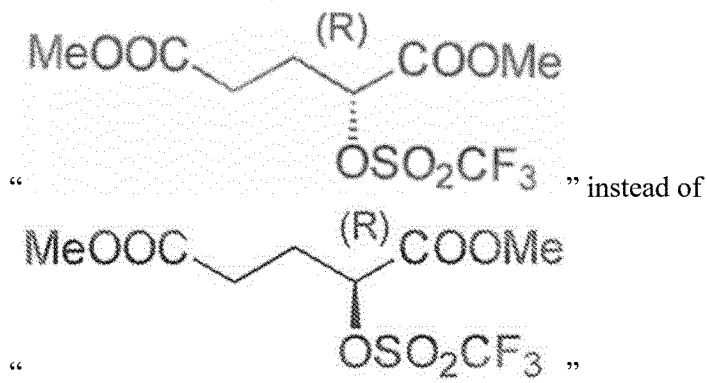 " instead of

"  "

Claim 2 at Column 44, Line 24 should read "complex by hydrolyzing the compound of formula XV and adding a gadolinium salt." instead of "complex."

Signed and Sealed this
Seventh Day of January, 2025

Derrick Brent
*Acting Director of the United States Patent and Trademark Office*